United States Patent
Sasai et al.

(10) Patent No.: US 10,808,224 B2
(45) Date of Patent: Oct. 20, 2020

(54) METHOD FOR CULTURING STEM CELL

(71) Applicants: RIKEN, Wako-shi, Saitama (JP); Sumitomo Chemical Company, Limited, Tokyo (JP)

(72) Inventors: Yoshiki Sasai, Wako (JP); Hidetaka Suga, Wako (JP)

(73) Assignees: RIKEN, Wako (JP); Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/354,864

(22) PCT Filed: Oct. 31, 2012

(86) PCT No.: PCT/JP2012/078250
§ 371 (c)(1),
(2) Date: Apr. 28, 2014

(87) PCT Pub. No.: WO2013/065763
PCT Pub. Date: May 10, 2013

(65) Prior Publication Data
US 2014/0308743 A1    Oct. 16, 2014

(30) Foreign Application Priority Data
Oct. 31, 2011    (JP) .................................. 2011-239803

(51) Int. Cl.
*C12N 5/079*    (2010.01)
*C12N 5/071*    (2010.01)
*A61K 35/30*    (2015.01)

(52) U.S. Cl.
CPC ............ *C12N 5/0618* (2013.01); *A61K 35/30* (2013.01); *C12N 5/0616* (2013.01); *C12N 2501/33* (2013.01); *C12N 2501/39* (2013.01); *C12N 2501/392* (2013.01); *C12N 2501/41* (2013.01); *C12N 2501/42* (2013.01); *C12N 2506/02* (2013.01)

(58) Field of Classification Search
CPC .............. A61K 2300/00; A61K 35/545; C12N 2501/41; A61L 27/3834; A61L 27/3895; A61L 2300/64; G01N 33/5073
See application file for complete search history.

(56) References Cited

U.S. PATENT DOCUMENTS

| | | | |
|---|---|---|---|
| 4,383,034 A | 5/1983 | Sugimoto | |
| 4,383,035 A | 5/1983 | Sugimoto | |
| 8,008,075 B2* | 8/2011 | Green ................. | C12N 5/0606 435/366 |
| 10,273,452 B2* | 4/2019 | Chambers ............... | A61P 5/00 |
| 2008/0044901 A1 | 2/2008 | Sasai et al. | |
| 2011/0091869 A1* | 4/2011 | Sasai .................... | C12N 5/0623 435/5 |

FOREIGN PATENT DOCUMENTS

| | | |
|---|---|---|
| JP | S57-043695 A | 3/1982 |
| JP | S57-043696 A | 3/1982 |
| JP | S58-069818 A | 4/1983 |
| JP | S58-071885 A | 4/1983 |
| JP | H09-509306 A | 9/1997 |
| WO | WO 2000/000646 A1 | 1/2000 |
| WO | WO 2005/123902 A1 | 12/2005 |
| WO | WO 2008/024832 A2 | 3/2008 |
| WO | WO 2008/035110 A1 | 3/2008 |
| WO | WO 2009/148170 A1 | 12/2009 |

OTHER PUBLICATIONS

Danjo et al. Subregional specification of embryonic stem cell-derived ventral telencephalic tissues by timed and combinatory treatment with extrinsic signals. JNS. 2011;31(5):1919-1933.*
U.S. Appl. No. 15/328,985 to Sasai et al; filed Jan. 25, 2017. (Year: 2017).*
Ozone et al., "Functional anterior pituitary generated in self-organizing culture of human embryonic stem cells," *Nature Communications*, 7: 10351 (Jan. 14, 2016).
Suga et al., *Nature*, 480(7375): 75-62 (2011).
Wataya et al., *Proc. Natl. Acad. Sci. USA*, 105(33): 11796-11801 (2008).
Japanese Patent Office, International Search Report in International Search Report in International Patent Application No. PCT/JP2012/078250 (Feb. 5, 2013).
Papageorgiou et al., *Endocrinology*, 148(9): 4509-4522 (2007).
Suga, Hidetaka, *Neuroendocrinology*, DOI: 10.1159/000369821 (Nov. 18, 2014).
Tabar, Viviane, *Cell Stem Cell*, 9(6): 490-491 (2011).
Zeng et al., *Medical Hypotheses*, 77(4): 680-681 (2011).
Ulloa et al., "Morphogens and the Control of Cell Proliferation and Patterning in the Spinal Cord," *Cell Cycle*, 6(21): 2640-2649 (2007).
Wang et al., "Bone Morphogenetic Protein (BMP) signaling in development and human diseases," *Genes Dis.*, 1(1): 87-105 (2014).
Bharti et al., "Lack of ventral anterior homeodomain transcription factor VAX1 leads to induction of a second pituitary," *Development*, 138(5): 873-878 (2011).

* cited by examiner

*Primary Examiner* — Allison M Fox
(74) *Attorney, Agent, or Firm* — Leydig, Voit & Mayer, Ltd.

(57) ABSTRACT

The present invention provides a method of obtaining aggregates containing a rostral hypothalamus tissue and a rostral head ectodermal tissue, a hypophysis precursor tissue and a hypophysis hormone producing cell, by using a serum-free medium (preferably substantially free of growth factor and insulins), forming homogeneous aggregates of stem cells from pluripotent stem cells such as ES cell and the like, which are plated at a high cell concentration, and subjecting the formed aggregates to floating-culture.

24 Claims, 7 Drawing Sheets

METHOD FOR CULTURING STEM CELL

CROSS-REFERENCE TO RELATED APPLICATIONS

This patent application is the U.S. national phase of International Patent Application No. PCT/JP2012/078250, filed Oct. 31, 2012, which claims the benefit of Japanese Patent Application No. 2011-239803, filed on Oct. 31, 2011, which are incorporated by reference in their entireties herein.

TECHNICAL FIELD

The present invention relates to a method of inducing differentiation of stem cells into an embryoid body comprising a central nervous tissue and a non-neural head ectoderm tissue in vitro and the like. Moreover, the present invention particularly relates to a method of inducing differentiation into a hypophysis precursor tissue and various hypophysis hormone-producing cells as a central nervous tissue in vitro and the like.

BACKGROUND ART

To date, some culturing methods for inducing nerve differentiation of pluripotent stem cells such as ES cells have been known (non-patent documents 1-4, patent documents 1-3).

The present inventors previously showed that dispersed floating-culture in a serum-free medium (the SFEB method) is effective as a method of inducing nerve differentiation of pluripotent stem cells such as animal or human ES cells into nerves (non-patent documents 3 and 4 and patent document 1). Thereafter, the present inventors found a method of efficiently inducing differentiation of pluripotent stem cells such as ES cells and the like into cerebral cortex tissue, hypothalamus neurons, progenitor cells thereof and the like by forming homogeneous aggregates of stem cells in a serum-free medium, and subjecting the aggregates to floating-culture (the SFEBq method) (non-patent document 5 and patent document 3).

In vertebrata, pituitary gland and sensory organs (olfactory epithelium, crystalline lens, inner ear and the like) are known to develop from a placode formed in a non-neural head ectoderm tissue facing a neural plate, via induction of placode, invagination of placode, cell differentiation, and morphogenesis.

Of these, pituitary gland is an endocrine organ that produces and secretes many hormones. Pituitary gland is largely divided into adenohypophysis and neurohypophysis (also called posterior pituitary), and adenohypophysis is further divided into anterior pituitary and intermediate pituitary (intermedia). Adenohypophysis comprises plural kinds of cells that produce and secrete pituitary hormones.

The adenohypophysis is derived from Rathke's pouch generated by invagination of primary oral cavity. In mammalian initial development, anterior pituitary primordium is formed as a placode in a non-neural head ectoderm (rostral non-neural head ectoderm) adjacent to the rostral of the anterior neural plate boundary, and the placode invaginates to form Rathke's pouch. The Rathke's pouch thereafter separates from ectoderm to become an epithelial pouch vesicle. Then, the anterior wall of the pouch vesicles becomes anterior pituitary and the posterior wall becomes intermediate pituitary.

On the other hand, the neurohypophysis (posterior pituitary) is formed from a protrusion in the bottom part of the third ventricle. Axon extends from the neurosecretory neuron cells in the supraoptic nuclei and paraventricular nuclei of the hypothalamus to the posterior pituitary, and hormones (oxytocin and vasopressin) are axonally transported.

The studies heretofore have revealed that interactions of rostral hypothalamus and rostral non-neural head ectoderm are necessary for the induction of Rathke's pouch in the developmental stages (non-patent document 6).

As mentioned above, the late developmental processes of pituitary gland have been widely studied; however, specialization of pituitary primordium in the initial stages of ectoderm has not been elucidated as yet. Although methods for inducing differentiation into nerve cells such as cerebrum, hypothalamus and the like have been found to date (mentioned above), a method of developing a pituitary precursor tissue and various pituitary hormone-producing cells from pluripotent stem cells such as ES cells and the like in vitro (in vitro) is not known yet.

In addition, while treatment of diabetes using stem cells has also been considered before, the possibility of regenerative medicine taking note of functional disorders of hypothalamus-pituitary gland has hardly attracted attention to date.

DOCUMENT LIST

Patent Documents patent document 1: WO2005/123902
patent document 2: JP-A-2008-99662
patent document 3: WO2009/148170

Non-Patent Documents non-patent document 1: Watanabe, K. et al., Nature Biotechnology 25, 681-686 (2007)
non-patent document 2: Su, H.-L. et al., Developmental Biology 290, 287-296 (2006)
non-patent document 3: Ikeda, H. et al., Proc. Natl. Acad. Sci. USA 102, 11331-11336 (2005)
non-patent document 4: Watanabe, K. et al., Nature Neurosci. 8, 288-296 (2005)
non-patent document 5: Wataya, T. et al., Proc. Natl. Acad. Sci. USA 105, 11796-11801 (2008)
non-patent document 6: Bharti, K. et al., Development 138, 873-878 (2011)

SUMMARY OF THE INVENTION

Problems to be Solved by the Invention

The present invention aims to provide a method of inducing differentiation of a stem cell into an embryoid body (hereinafter to be also referred to as "aggregate") comprising a central nervous tissue and a non-neural head ectodermal tissue in vitro. In addition, the present invention particularly aims to provide a method of efficiently inducing differentiation into a pituitary precursor tissue and various pituitary hormone-producing cells as a central nervous tissue in vitro.

Means of Solving the Problems

The present inventors have conducted intensive studies in an attempt to solve the aforementioned problems and succeeded in reproducing the development of anterior pituitary in vitro and succeeded in inducing differentiation of pluripotent stem cells such as ES cells and the like into a pituitary precursor tissue and various pituitary hormone-producing cells. To be specific, they have further studied the conditions by using the SFEBq method disclosed in patent document 3 and non-patent document 5, and found for the first time the conditions capable of simultaneously inducing differentiation into both a central nervous tissue and a non-neural head ectodermal tissue, particularly a rostral hypothalamus tissue and a rostral non-neural head ectodermal tissue which is a sheet-like continuous epithelium, in one aggregate. Furthermore, they have induced a pituitary precursor tissue (Rathke's pouch-like tissue) from this aggregates, and succeeded in inducing various pituitary hormone-producing cells from this tissue. Based on such findings, the present inventors have completed the following invention.

[1] A method of producing an aggregate comprising both a hypothalamus tissue and a non-neural head ectoderm, comprising a step of forming an aggregate of stem cells in a serum-free medium, and
a step of floating-culturing the formed aggregate in a serum-free medium.
[2] The production method of [1], wherein the serum-free medium used for the floating-culturing comprises an Shh signal promoter.
[3] The production method of [2], wherein the Shh signal promoter is SAG.
[4] The production method of any of [1] to [3], wherein the serum-free medium used for the floating-culturing comprises a BMP signal promoter.
[5] The production method of [4], wherein the BMP signal promoter is BMP2 and/or BMP4.
[6] The production method of any of [1] to [5], wherein the hypothalamus tissue and non-neural head ectoderm are a rostral hypothalamus tissue and a rostral non-neural head ectodermal tissue which is a sheet-like continuous epithelium.
[7] The production method of [6], wherein the rostral hypothalamus tissue is Rx-positive.
[8] The production method of [6], wherein the rostral non-neural head ectodermal tissue which is a sheet-like continuous epithelium is Pitx1-positive.
[9] The method of [1], wherein the serum-free medium does not substantially comprise a Nodal signal promoter, a Wnt signal promoter, an FGF signal promoter, a BMP signal promoter, retinoic acid and insulin.
[10] The production method of any of [1] to [9], wherein the stem cells are derived from human.
[11] The production method of any of [1] to [10], wherein the aggregate comprising both a hypothalamus tissue and a non-neural head ectoderm further comprises Lim3-positive cells.
[12] The production method of [11], wherein the Lim3-positive cells form an epithelial pouch vesicle in the aggregate.
[13] The production method of [1], wherein an expression of an endogenous growth factor in the aggregate of stem cells is increased by the floating-culturing.
[14] The production method of [13], wherein the endogenous growth factor is BMP2 and/or BMP4.
[15] The production method of [14], wherein expression of the BMP2 and/or BMP4 increases not less than 2-fold at an mRNA level as compared to a case wherein a aggregate of stem cells is formed at a low cell concentration.
[16] A method of producing an adrenocorticotropic hormone-producing cell, comprising a step of further floating-culturing the aggregate comprising both a hypothalamus tissue and a non-neural head ectoderm produced by the production method of any of [1] to [15], in a serum-free medium comprising a Notch signal inhibitor.
[17] The production method of [16], wherein the Notch signal inhibitor is DAPT.
[18] A method of improving deficiency of adrenocorticotropic hormone secretion in a subject, comprising transplanting adrenocorticotropic hormone-producing cells produced by the method of [16] or [17] to the subject.
[19] A method of producing a growth hormone-producing cell, comprising a step of further floating-culturing the aggregate comprising both a hypothalamus tissue and a non-neural head ectoderm produced by the production method of any of [1] to [15], in a serum-free medium comprising glucocorticoid.
[20] The production method of [19], wherein the serum-free medium further comprises insulin.
[21] The production method of [19] or [20], comprising a step of floating-culturing the aggregate comprising both a hypothalamus tissue and a non-neural head ectoderm in a serum-free medium comprising a GSK3β inhibitor before or simultaneously with the step of floating-culturing in a serum-free medium comprising glucocorticoid.
[22] The production method of [21], wherein the GSK3β inhibitor is BIO.
[23] A method of improving deficiency of growth hormone secretion in a subject, comprising transplanting growth hormone-producing cells produced by the production method of any of [19] to [22] to the subject.
[24] A method of producing prolactin-producing cell, comprising a step of further floating-culturing the aggregate comprising both a hypothalamus tissue and a non-neural head ectoderm produced by the production method of any of [1] to [15] in a serum-free medium comprising an estrogen.
[25] The production method of [24], wherein the serum-free medium further comprises insulin.
[26] The production method of [24] or [25], comprising a step of floating-culturing the aggregate comprising both a hypothalamus tissue and a non-neural head ectoderm in a serum-free medium comprising a GSK3β inhibitor before or simultaneously with the step of floating-culturing in a serum-free medium comprising an estrogen.
[27] The production method of [26], wherein the GSK3β inhibitor is BIO.
[28] A method of improving deficiency of prolactin secretion in a subject, comprising transplanting prolactin-producing cells produced by the production method of any of [24] to [27] to the subject.
[29] A method of producing a follicle-stimulating hormone, luteinizing hormone and/or thyroid-stimulating hormone-producing cell, comprising a step of further floating-culturing the aggregate comprising both a hypothalamus tissue and a non-neural head ectoderm produced by the production method of any of [1] to [15], in a stromal cell-conditioned medium obtained by cultivating stromal cells in a serum-free medium.
[30] The production method of [29], wherein the stroma cell is PA6 cell.
[31] A method of improving deficiency of secretion of follicle-stimulating hormone, luteinizing hormone or thyroid-stimulating hormone in a subject, comprising transplanting follicle-stimulating hormone-, luteinizing hormone- or thyroid-stimulating hormone-producing cells produced by the method of [29] or [30] to the subject.
[32] A method of producing an aggregate comprising both a central nervous tissue and a non-neural head ectodermal tissue, comprising a step of forming an aggregate of stem cells in a serum-free medium, and a step of floating-culturing the formed aggregate in a serum-free medium.

[33] A method of producing a placode that forms olfactory epithelium, crystalline lens or inner ear, which comprises self-forming the placode in the aggregate of [32].

Effect of the Invention

According to the method of the present invention, pluripotent stem cells such as ES cells and the like can be induced to differentiate into an aggregates comprising a central nervous tissue and a non-neural head ectodermal tissue, specifically an aggregates comprising a rostral hypothalamus tissue and a rostral head ectodermal tissue which is a sheet-like continuous epithelium, or a pituitary precursor tissue in vitro, and can be further induced to differentiate into various pituitary hormone-producing cells. The pituitary gland is a central endocrine organ that produces and secretes various hormones, and abnormal hormone secretion exerts a grave influence on the live body. Therefore, the aggregates, pituitary precursor tissues and pituitary hormone-producing cells obtained by the method of the present invention can be utilized for the treatment and the like of the diseases caused by the deficiency of secretion of pituitary hormones and the diseases causing deficiency of a pituitary hormone secretion.

BRIEF DESCRIPTION OF THE DRAWINGS

FIG. 3a shows differentiation into each pituitary hormone-producing cells. FIG. 3b shows enhanced Tbx19 expression due to DAPT treatment with the hypophysis precursor tissue obtained by SAG treatment (day 20) (DAPT treatment (days 18-19)/BIO treatment (days 16-18)). FIG. 3c shows percentages of ACTH$^+$ cells in non-neural (N-cad$^-$) cells on day 22 (DAPT treatment (days 18-19)/BIO treatment (days 16-18)). FIG. 3d-g shows expression of marker genes in SAG$^+$ DAPT-treated aggregates. Red: ACTH, green: E-cadherin (e)/neurofilament (f)/PC2 (g). FIG. 3h shows attenuated Tbx19 and ACTH expression by shRNA-mediated knockdown of lim3 by deoxycycline (Dox) treatment. FIG. 3i shows expression of Rx, lim3 and ACTH of LCA+ SAG-treated SFEBq aggregates with DAPT treatment. FIG. 3j shows schematic of corticotroph generation from the ESC-derived pouch. FIG. 3k shows graph showing influences of DAFT, BIO and IWP2 on Pitx1 expression (day 26)

FIGS. 3n and 3o show generation of Prolactin$^+$ cells in LCA+ SAG aggregates (day 33) (estradiol and insulin were added on days 20-30). FIGS. 3p-3s show generation of LH$^+$ cells, FSH$^+$ cells, and TSH$^+$ cells in LCA+ SAG aggregates (day 33) (PA6-conditioned medium (acclimation medium) was added from day 10). Scale bars, 20 μm (d, e); 50 μm (f, g); 100 μm (m, o, q, r, s).

DESCRIPTION OF EMBODIMENTS

Figure 1:
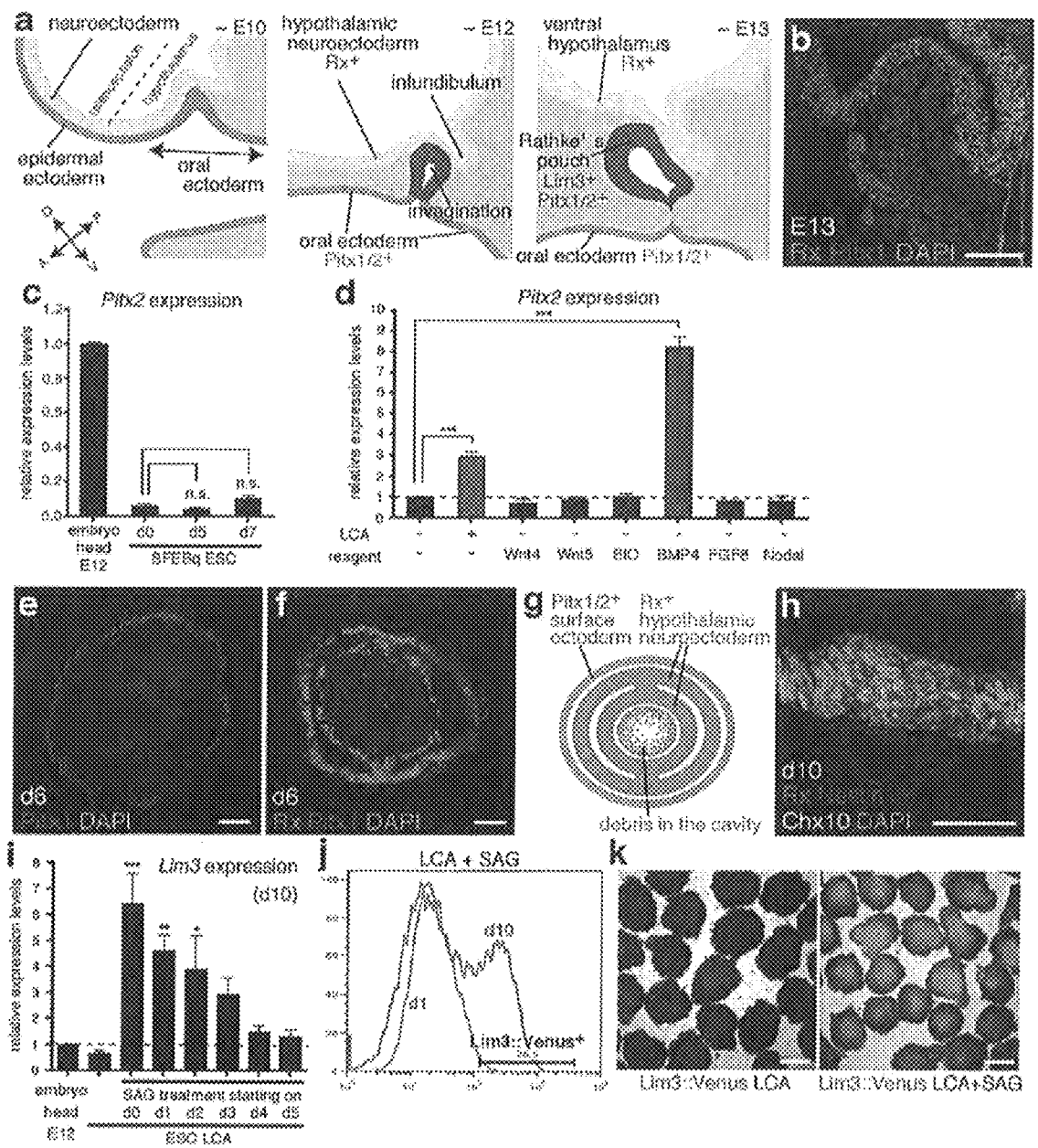
FIG. 1a shows schematic (sagittal view) of in vivo pituitary development.
FIG. 1b shows gene expression in Rathke's pouch and Rx expression in the adjacent ventral hypothalamic tissue in vivo on E13 (hypothalamus marker Rx: green; non-neural head ectoderm marker Pitx1: read).
FIG. 1c shows expression level of Pitx2 in SFEBq/CDM-cultured ESCs (3000 cells/aggregate). Little expression of Pitx2 was observed.
FIG. 1d shows elevation of Pitx2 expression in SFEBq/CDM-cultured ESCs under the large cell-aggregation (LCA; starting with 10000 cells) condition (red) or treated with BMP4 (blue).
FIGS. 1e and 1f shows expression of Pitx1 (red), and Rx (green, f) in aggregates obtained by plating mouse ES cells at high concentration (LCA condition) and culturing by SFEBq/gfCDM method.
FIG. 1g shows schematic of the FIG. 1f result.
FIG. 1h shows that Rx$^+$ tissue is Chx10$^-$/Nestin$^+$.
FIG. 1i shows a graph indicating an influence of a timing of addition of Shh signal accelerator SAG on lim3 expression level.
FIG. 1j shows FACS analysis showing a lim3::venus$^+$ population in LCA aggregates with SAG treatment (green).
FIG. 1k shows comparison of lim3 expression in LCA aggregates with (right) or without (left) SAG treatment. Scale bars, 100 μm (b,e,f); 50 μm (h); 500 μm (k).

The present invention is explained in detail in the following.

(1) Tissues and Cells Obtained by the Production Method of the Present Invention (A) Aggregates Comprising Central Nervous Tissue and Non-Neural Head Ectodermal Tissue According to the production method of the present invention (sometimes to be referred to as a differentiation induction method), differentiation into an aggregate comprising both a central nervous tissue and a non-neural head ectodermal tissue, particularly a rostral hypothalamus tissue (also simply referred to as a hypothalamus tissue) and a rostral non-neural head ectodermal tissue which is a sheet-like continuous epithelium (also simply referred to as a non-neural head ectodermal tissue) can be induced. The aggregate comprising a rostral hypothalamus tissue and a rostral non-neural head ectodermal tissue which is a sheet-like continuous epithelium is, for example, a cell aggregate comprising a rostral non-neural head ectodermal tissue composed of sheet-like continuous epithelium-like monolayer of Pitx1-positive cells present on the contact surface with a culture medium, and a rostral hypothalamus tissues composed of Rx-positive cells inside of the rostral non-neural head ectodermal tissue. In the differentiation induction method of the present invention, since both tissues of a central nervous tissue and a non-neural head ectodermal tissue are simultaneously formed in one aggregate (specifically, a sheet-like non-neural head ectodermal tissue is formed on the outside of the central nervous tissue in one aggregate), these tissues can interact topically.

It is known that interaction of rostral hypothalamus tissue and rostral non-neural head ectodermal tissue is necessary for inducing Rathke's pouch (precursor tissue of pituitary gland) in the developmental process of an individual (Bharti et al (2011) Development 138, 873-878).

For example, when a rostral non-neural head ectodermal tissue which is a sheet-like continuous epithelium is formed on the outside of a rostral hypothalamus tissue in one aggregate, these tissues can topically interact and induce a pituitary precursor tissue, and further, hypophysis hormone-producing cells.

In addition, interaction of central nervous tissue and non-neural head ectodermal tissue is also necessary for the formation of an head ectodermal placode that forms a sensory organ. To be specific, olfactory epithelium is developed via a placode formed by an interaction between a cerebrum tissue and a rostral non-neural head ectodermal tissue (Olfactory placode); a crystalline lens is developed via a placode (Lens placode) formed by an interaction between a retina tissue and a non-neural head ectodermal tissue; and an inner ear is developed via a placode (Otic placode) formed by an interaction between a mesencephalon tissue and a non-neural head ectodermal tissue.

That is, when a combination of the aforementioned tissues is formed with the aforementioned constitution in one aggregate, these tissues can topically interact, which leads to the formation of each placode and the development of each sensory organ.

Whether the cells in the aggregate belong to a central nervous tissue or a non-neural head ectodermal tissue can be judged based on the gene expression profile of the central nervous tissue and the non-neural head ectodermal tissue, which is observed in a normally-developed live body. Specific gene expression profile is described in the following (D). In one embodiment, the rostral hypothalamus tissue is a Rx$^+$, N-cadherin$^+$, Sox$^{1+}$ nerve tissue. In one embodiment, the rostral hypothalamus tissue is a Rx$^+$, Chx10$^-$, NRx2.1$^+$, Nestin$^+$ nerve tissue. In one embodiment, the rostral head ectodermal tissue (rostral non-neural head ectoderm) is a sheet-like continuous epithelial tissue formed on a surface layer of the aggregate, which is composed of Pitx1-positive, N-cadherin$^+$ monolayer cells.

(B) Rathke's Pouch-Like Tissue

In the development of a live body, adenohypophysis (anterior pituitary and intermediate pituitary) is induced from a tissue called Rathke's pouch. The Rathke's pouch is formed in a very early stage of ontogenesis by invagination of a placode formed in rostral non-neural head ectoderm, and is subsequently separated from the ectoderm to be an epithelial pouch vesicle.

According to the method of the present invention, a pouch vesicle having an epithelial structure and polarity similar to those of Rathke's pouch is formed in the above-mentioned aggregate comprising a rostral hypothalamus tissue and a rostral non-neural head ectodermal tissue. The pouch vesicle is present in the vicinity of the hypothalamus tissue, like the Rathke's pouch in a live body, and is also adjacent to the rostral non-neural head ectodermal tissue. That is, the method of the present invention can reproduce the microenvironment in the development of pituitary gland in a live body (see FIG. 2*p*).

Therefore, the "Rathke's pouch-like tissue" or "pituitary precursor tissue" in the present invention is defined by the characteristics, for example, having morphological characteristics (concave or pouch vesicle) similar to those of Rathke's pouch observed in a normally developed live body, being present in the vicinity of hypothalamus tissue and rostral non-neural head ectodermal tissue, having the same gene expression profile as that of Rathke's pouch in a live body, and the like. The specific gene expression profiles are described in the following (D). In one embodiment, the Rathke's pouch-like tissue is a Lim3-positive epithelial pouch vesicle.

(C) Pituitary Hormone-Producing Cells

Anterior pituitary secretes adrenocorticotropic hormone (ACTH), growth hormone (GH), thyroid-stimulating hormone (TSH), prolactin (PRL), follicle-stimulating hormone (FSH), and luteinizing hormone (LH) (anterior pituitaryhormone), and intermediate pituitary secretes melanocyte-stimulating hormone (MSH) (intermediate pituitary hormone). MSH is one of the ACTH related peptides, and is formed by enzymatic degradation of propiomelanocortin which is a common precursor with ACTH. On the other hand, since oxytocin (OX) and vasopressin (VP), which are hormones secreted by posterior pituitary, are produced in hypothalamus, they are not included in the pituitary hormone in the present specification. The pituitary hormone in the present specification refers to anterior pituitary hormone.

(i) Adrenocorticotropic Hormone (ACTH)

It is also referred to as corticotropin. It is a peptide hormone having 39 amino acids and secreted from adrenocorticotropic hormone-producing and secreting cells (corticotrophs) in the anterior pituitary. ACTH shows a glucocorticoid secretagogue action. Secretion of ACTH is promoted by corticotropin-releasing hormone (CRH) secreted from hypothalamus, and negatively feedbacked by glucocorticoid.

(ii) Growth Hormone (GH)

It is also referred to as somatotropin. It is secreted from growth hormone-producing and secreting cells (somatotrophs) in anterior pituitary. In the case of human, it is a peptide hormone having 191 amino acids. GH shows various biological activities such as a promoting action on protein synthesis and cartilage growth, lipolysis action and the like. Secretion of GH is stimulated by a growth hormone-releasing hormone (GHRH) secreted from hypothalamus, and suppressed by somatostatin. Secretion of GH is also negatively feedbacked by GH itself and IGF-1.

(iii) Prolactin (PRL)

It is a peptide hormone mainly secreted from prolactin-producing and secreting cells (lactotrophs) in anterior pituitary, and having 199 amino acids. In human, PRL promotes milk secretion and differentiation and development of mammary gland in the presence of estrogen and shows an action of pregnancy maintenance and the like. Secretion of PRL is stimulated by prolactin releasing factors (PRFs) (e.g., thyroid-stimulating hormone releasing hormone (TRH), vasopressin, vasoactive intestinal peptide (VIP), peptide histidine isoleucine (PHI)) and TRH, and suppressed by prolactin inhibitory factors (PIFs) (e.g., dopamine, γ-amino butyric acid (GABA)).

(iv) Luteinizing Hormone (LH)

It is one kind of gonadotropic hormones (gonadotropins), and is a glycoprotein composed of α-subunit and β-subunit, which is secreted from gonadotropic hormone-producing and secreting cells (gonadotrophs) in anterior pituitary. In female, LH acts together with FSH on developing follicle to grow follicle, promotes ovulation and luteinization, stimulates production of estrogen and progesterone, and plays an important role in the formation of menstrual cycle. In male, it acts on Leydig cells in testis to promote secretion of testosterone. Secretion of LH is also promoted by gonadotropin-releasing hormone (GnRH) secreted from hypothalamus.

(v) Follicle-Stimulating Hormone (FSH)

It is one kind of gonadotropic hormones (gonadotropins), and is a glycoprotein composed of α-subunit and β-subunit, which is secreted from gonadotropic hormone-producing and secreting cells (gonadotrophs) in anterior pituitary. Secretion of FSH is also promoted by gonadotropin-releasing hormone (GnRH) secreted from hypothalamus. In female, FSH acts on ovary to make primordial follicle into developing follicle, acts together with LH to grow same into mature follicle, and promotes secretion of estrogen from follicle. When estrogen increases, the secretion of GnRH is suppressed by the feedback to hypothalamus and secretion of FSH is also suppressed. When estrogen further increases, GnRH increases due to a positive feedback to hypothalamus and pituitary gland. In male, it acts on Sertoli cells in testis to promote secretion of testosterone and promotes spermatogenesis.

(vi) Thyroid-Stimulating Hormone (TSH)

It is a glycoprotein composed of α-subunit and β-subunit (α-subunit is common with LH, FSH), which is secreted from thyroid-stimulating hormone-producing and secreting cells (thyrotrophs) in anterior pituitary. TSH acts on thyroid gland to promote production or secretion of thyroid gland hormone. Secretion of TSH is stimulated by thyrotropin-releasing hormone (TRH) secreted from hypothalamus, and negatively feedbacked by thyroid hormone.

A cell capable of producing and secreting any of these pituitary hormones, which is obtained by the differentiation induction method of the present invention, is generically referred to as a "pituitary hormone-producing cell" in the present specification.

Examples of the disease caused by failure in the production or secretion of any of the above-mentioned pituitary hormones include hypoadrenocorticism, growth hormone deficiency dwarfism, adult-onset GH deficiency, pituitary dwarfism, cretinism, infertility and the like. In panhypopituitarism (including empty sella syndrome, hypophysis apoplexy, postoperative hypophysis damage), partial hypopituitarism, and isolated anterior pituitary hormone deficiency (specifically, isolated ACTH deficiency, isolated growth hormone deficiency, isolated TSH deficiency, isolated prolactin deficiency, isolated gonadotropic hormone deficiency), a failure occurs in the production or secretion of one or all of the above-mentioned hypophysis hormones.

(D) Identification of Tissue and Cell

The tissues or cells obtained by the method of the present invention can be confirmed as to which tissues or cells they have differentiated into, by using, as an index, the presence or absence of expression of a marker gene, or release of a pituitary hormone into a medium or intracellular accumulation of the precursor protein in the case of pituitary hormone-producing cells, and the like, or combining them as necessary. In addition, the obtained tissues or cells can also be specified by observing the morphology of the tissues and cells. Furthermore, a desired particular tissue or cell can also be isolated based on such marker expression patterns and tissue or cell morphology.

Examples of the markers used in the present invention include, but are not limited to, pituitary hormones such as ACTH, GH, PRL, LH, FSH, TSH and the like, N-cadherin, Nkx2.1 (neural marker), Sox1 (neural ectoderm marker), nestin (neural ectoderm marker), neurofilament and NSE (neuron-specific enolase) (neuron marker), Rx (hypothalamus marker), Pitx1 and Pitx2 (non-neural head ectoderm marker), Chx10 (retinal marker), Lim3 (initial pituitary/pituitary precursor tissue marker), Islet1 and 2 (late Rathke's pouch marker), E-cadherin (epithelial cell marker), Prop1 and Pit1 (markers specific to gonadotroph, somatotroph, lactotroph or caudomedial thyrotroph precursor), Tbx19 (marker specific to corticotroph), PC2 (melanotropic lineage marker) and the like. The identity of the obtained cell can be specified by appropriately combining the presence or absence of the expression of these and other marker genes.

The tissues or cells obtained by the differentiation induction method of the present invention can be characterized according to the gene expression profile of a tissue or cell actually present in a live body.

For example, by definition using the above-mentioned markers, the cell of rostral hypothalamus tissue is $Rx^+$, preferably $Rx^+$, $N-cadherin^+$, $nestin^+$, $Nkx2.1^+$, $Chx10^-$. The cell of rostral head ectodermal tissue (rostral non-neural head ectoderm) is $Pitx1^+$, preferably $Pitx1^+$, $Pitx2^+$, $E-cadherin^+$. The cell of pituitary precursor tissue (Rathke's pouch-like tissue) is $Lim3^+$, $Pitx1^+$, $Pitx2^+$, $Isl1^+$, $E-cadherin^+$ (which matches the expression profile of pituitary primordium). The pituitary (non-neural) hormone-producing cell is neurofilament⁻, NSE⁻. The pituitary ACTH-producing cell is ACTH$^+$, Tbx19$^+$, PC2$^-$, and other pituitary hormone-producing cells are Tbx19$^-$. The MSH-producing cell of intermediate pituitary is ACTH$^-$, Tbx19$^+$, PC2$^+$. The pituitary GH-producing cell, PRL-producing cell and TSH-producing cell are differentiated into each pituitary hormone-producing cell via a Pitx1$^+$ intermediate precursor.

According to the method of the present invention, differentiation into the above-mentioned central nervous tissue and non-neural head ectodermal tissue, for example, a rostral hypothalamus tissue and a rostral head ectodermal tissue (rostral non-neural head ectoderm), is simultaneously induced in one aggregate. In this case, an aggregate wherein a rostral head ectodermal tissue (non-neural head ectoderm) is present on a surface layer, and a central nervous tissue (rostral hypothalamus tissue) is present inside thereof is obtained.

According to the further method of the present invention, a Rathke's pouch-like tissue is formed in an aggregate. The pouch vesicle shows the same marker expression as pituitary precursor tissues and has a morphologically similar epithelial structure and polarity. Furthermore, like the pituitary precursor tissue (Rathke's pouch) in a live body, it is present in the vicinity of an Rx-positive hypothalamus tissue, and is formed also in adjacency to a rostral non-neural head ectodermal tissue. This indicates that the differentiation induction method of the present invention imitates the microenvironment in the development of a pituitary precursor tissue in the process of embryogenic development. Therefore, the Rathke's pouch-like tissue is also referred to as a pituitary precursor tissue in the present invention.

In the case of pituitary hormone-producing cells, differentiation into each pituitary hormone-producing cell can be confirmed by using the release of each of ACTH, GH, PRL, LH, FSH and TSH into medium, intracellular accumulation of precursor proteins thereof and the like as indices.

When the expression of marker genes specific to each hypophysis hormone-producing cell is used as an index, ACTH-producing cell can be characterized by the expression of ACTH and Tbx19 as an index, GH-producing cell can be characterized by the expression of GH as an index, PRL-producing cell can be characterized by the expression of PRL as an index, TSH-producing cell can be characterized by the expression of TSH as an index, FSH-producing cell can be characterized by the expression of FSH as an index, and LH-producing cell can be characterized by the expression of LH as an index. While pituitary hormones are also secreted from neuron, each pituitary hormone-producing cell obtained by the production method of the present invention can be distinguished from such neuron in that neural markers NSE and neurofilament are negative.

The expression of marker gene is analyzed by performing quantitative PCR, for example, 7500 Fast Real-Time PCR System (Applied Biosystems), according to the instructions of the manufacturer, and normalizing the data by GAPDH expression. The method of quantitative PCR is known to those of ordinary skill in the art. Alternatively, the cells may be manipulated (knocked in) to allow for expression of a desired marker gene as a fusion protein of a marker gene product and GFP, venus and the like. It is also possible to detect protein expression by using an antibody specific to the marker gene product.

These proteins can be detected by immunostaining or radioimmunoassay. In addition, other pituitary hormone production can also be assayed similarly using an antibody and the like specific to the hormone to be produced and the like. Such method is known to those of ordinary skill in the art.

(2) Stem Cells

A "stem cell" refers to a cell capable of retaining a constant potential for differentiation even after undergoing cell division. Examples of the stem cells include embryonic stem cells (ES cells) with pluripotency derived from a fertilized egg or a clone embryo, somatic stem cells and pluripotent stem cells that are present in tissues in a live body, hepatic stem cells, dermal stem cells, and germ stem cells that serve as the bases for respective tissues, pluripotent stem cells derived from a germ stem cell, pluripotent stem cells derived from a somatic cell that are obtained by nuclear reprogramming, and the like.

In particular, a "pluripotent stem cell" refers to a stem cell that permits cultivation in vitro, and having the potential for differentiating into all cells, but the placenta, constituting the body (tissues derived from the three germ layers of the embryo (ectoderm, mesoderm, endoderm)) (pluripotency); embryonic stem cells are also included therein. A "pluripotent stem cell" can be obtained from a fertilized egg, a clone embryo, a germ stem cell, or a stem cell in a tissue. Also included are cells having differentiation pluripotency similar to that of embryonic stem cells, conferred artificially by transferring several different genes to a somatic cell (also referred to as induced pluripotent stem cells). Pluripotent stem cells can be prepared by a method known per se. Available methods include, for example, methods described in Cell 131(5), pp. 861-872, Cell 126(4), pp. 663-676 and elsewhere.

As stem cells, for example, cells derived from a warm-blooded animal, preferably from a mammal, can be used. Mammals include, for example, laboratory animals, including rodents such as mice, rats, hamsters and guinea pigs, and rabbits; domestic animals such as pigs, cattle, goat, horses, and sheep; companion animals such as dogs and cats; primates such as humans, monkeys, orangutans, and chimpanzees.

Examples of stem cells that are specifically used in a method of the present invention include embryonic stem cells of a mammal or the like established by culturing a pre-implantation early embryo (hereinafter, abbreviated as "embryonic stem cells I"), embryonic stem cells established by culturing an early embryo prepared by nuclear-transplanting the nucleus of a somatic cell (hereinafter, abbreviated as "embryonic stem cells II"), induced pluripotent stem cells (iPS cells) established by transferring several different genes to a somatic cell, and/or acting a compound, and pluripotent stem cells prepared by modifying a gene on a chromosome of embryonic stem cells I, embryonic stem cells II or iPS cells using a gene engineering technique (hereinafter, abbreviated as "modified pluripotent stem cells").

More specifically, embryonic stem cells I include embryonic stem cells established from an inner cell mass that constitutes an early embryo, EG cells established from a primordial germ cell, cells isolated from a cell population possessing the pluripotency of pre-implantation early embryos (e.g., primordial ectoderm), cells obtained by culturing these cells, and the like.

Embryonic stem cells I can be prepared by culturing a pre-implantation early embryo according to a method described in the literature (Manipulating the Mouse Embryo A Laboratory Manual, Second Edition, Cold Spring Harbor Laboratory Press (1994)).

Embryonic stem cells II can be prepared using, for example, methods reported by Wilmut et al. (Nature, 385, 810 (1997)), Cibelli et al. (Science, 280, 1256 (1998)), Akira Iritani et al. (Protein, Nucleic Acid and Enzyme, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000)) and others, for example, as described below.

By extracting the nucleus of a mammalian cell and then reprogramming the nucleus (an operation to return the nucleus to a state to resume development), initiating development using a method involving injection into an enucleated unfertilized egg of a mammal, and culturing the egg that has started development, an egg that has the nucleus of another somatic cell, and has begun normal development, can be obtained.

A plurality of methods of reprogramming the nucleus of a somatic cell are known. For example, the nucleus can be reprogrammed by changing the medium used to culture the nucleus donor cell from a medium comprising 5 to 30%, preferably 10%, of fetal bovine serum (e.g., M2 medium) to an oligotrophic medium comprising 0 to 1%, preferably 0.5%, of fetal bovine serum, and culturing the cell for 3 to 10 days, preferably 5 days, to induce the cell cycle into a resting phase state (G0 stage or G1 stage).

The nucleus can also be reprogrammed by injecting the nucleus of the nucleus donor cell into an enucleated unfertilized egg of a mammal of the same species, and culturing the cell for several hours, preferably for about 1 to 6 hours.

The reprogrammed nucleus is able to begin development in the enucleated unfertilized egg. A plurality of methods of allowing the reprogrammed nucleus to begin development in the enucleated unfertilized egg are known. By transplanting a nucleus reprogrammed by inducing the cell cycle to a resting phase state (phase G0 or phase G1) into an enucleated unfertilized egg of a mammal of the same species by the electrofusion method and the like, the egg can be activated and allowed to begin development.

A nucleus reprogrammed by injecting the nucleus into an enucleated unfertilized egg of a mammal of the same species is transplanted back to an enucleated unfertilized egg of a mammal of the same species by a method using a micromanipulator or the like, and stimulated with an egg activator (e.g., strontium and the like), and thereafter treated with an inhibitor of cell division (e.g., cytochalasin B and the like) to suppress the release of the second polar body, whereby development can be initiated. This method is suitable when the mammal is, for example, a mouse or the like.

Provided that an egg once began to develop is obtained, embryonic stem cells can be acquired using publicly known methods described in Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Preparation of Mutant Mice Using ES Cells, Yodosha (1995) and the like.

An iPS cell can be produced by transferring, for example, Oct3/4, Sox2 and Klf4 (c-Myc or n-Myc further added as required) to a somatic cell (e.g., fibroblast, dermal cell and the like) (Cell, 126: p. 663-676, 2006; Nature, 448: p. 313-317, 2007; Nat Biotechnol, 26: p. 101-106, 2008; Cell 131: 861-872, 2007). It can also be produced by introducing Oct3/4 and Sox2, (further Klf4 as necessary), reacting same with a histone deacetylase inhibitor, valproic acid (Nature Biotechnology, 26: p. 1269-1275, 2008), but the method is not limited thereto.

Modified pluripotent stem cells can be prepared by using, for example, homologous recombination technology. Examples of the gene on the chromosome to be modified in preparing modified pluripotent stem cells, histocompatibility antigen genes, genes related to diseases based on disorders of nervous system cells, and the like. A modification of the target gene on the chromosome can be performed using methods described in Manipulating the Mouse Embryo A Laboratory Manual, Second Edition, Cold Spring Harbor Laboratory Press (1994); Gene Targeting, A Practical Approach, IRL Press at Oxford University Press (1993); Biomanual Series 8 Gene Targeting, Preparation of Mutant Mice Using ES Cells, Yodosha (1995) and the like.

Specifically, for example, a genomic gene of a target gene to be modified (e.g., histocompatibility antigen genes, disease-related genes and the like) is isolated, and a target vector for homologous recombination of the target gene is prepared using the genomic gene isolated. By transferring the target vector prepared to an embryonic stem cell, and selecting cells undergoing homologous recombination between the target gene and the target vector, stem cells having a modified gene on the chromosome can be prepared.

Methods of isolating a genomic gene of a target gene include publicly known methods described in Molecular Cloning, A Laboratory Manual, Second Edition, Cold Spring Harbor Laboratory Press (1989), Current Protocols in Molecular Biology, John Wiley & Sons (1987-1997) and elsewhere. A genomic gene of a target gene can also be isolated by using a genomic DNA library screening system (produced by Genome Systems), Universal GenomeWalker™ Kits (produced by CLONTECH) and the like.

Preparation of a target vector for homologous recombination of a target gene and efficient sorting of a homologous recombinant can be achieved by a method described in Gene Targeting, A Practical Approach, IRL Press at Oxford University Press (1993); Biomanual Series 8 Gene Targeting, Preparation of Mutant Mice Using ES Cells, Yodosha (1995) and elsewhere. The target vector used may be any one of the replacement type and the insertion type; useful methods of sorting include positive selection, promoter selection, negative selection, poly A selection and the like.

Available methods of selecting a desired homologous recombinant from among the sorted cell lines include Southern hybridization, PCR and the like, for genomic DNA.

Stem cells are available from specified organizations, and commercial products may be purchased. For example, the human embryonic stem cells KhES-1, KhES-2 and KhES-3 are available from the Institute for Frontier Medical Sciences, Kyoto University. Examples of mouse embryonic stem cells include EB5 cells and the like.

Stem cells can be cultured for maintenance by a method known per se. For example, stem cells can be maintained by cultivation without feeder cells with the addition of fetal bovine serum (FCS), Knockout™ Serum Replacement (KSR), and LIF.

(3) Formation of Homogenous Agglutinates of Stem Cells and Floating-Culture Thereof The step of forming homogenous aggregates of stem cells and the step of floating-culturing the aggregates to be used in the differentiation induction method of the present invention are almost the same as those in "The SFEBq method" disclosed in patent document 3 and non-patent document 5.

"Forming homogenous aggregates of stem cells" refers to forming qualitatively homogenous aggregates of stem cells by allowing "a given number of dispersed stem cells to aggregate quickly" in allowing stem cells to assemble and form aggregates of stem cells and culturing the aggregates (aggregate culture). The same refers particularly to promoting the epithelization of cells deriving from stem cells by allowing "the cells to aggregate quickly". Hence, as used herein, the term "to allow the cells to aggregate quickly" refers to forming with high reproducibility an epithelium-like structure in the cells produced by allowing stem cells to aggregate homogenously.

"Floating-culturing the homogenous aggregates of stem cells" or "Culturing the homogenous aggregates of stem cells as floating aggregates (also referred to as aggregate mass)" refers to culturing the stem cells assembled to form homogenous aggregates obtained in the above-mentioned step, in a culture medium under conditions that are non-adhesive to the cell culture vessel (herein, these steps are described as "the SFEBq method" together). When floating-culturing the stem cells, the culturing is preferably performed in the absence of feeder cells to facilitate the formation of suspended aggregates, and/or to achieve efficient induction of differentiation (e.g., induction of differentiation into ectodermal cells such as nervous system cells).

Any method may be employed to form homogenous aggregates of stem cells, as far as homogenous aggregates of stem cells are formed by allowing "the cells to aggregate quickly", and an epithelium-like structure of the cells produced from the stem cells is formed with high reproducibility; such methods include, for example, a method wherein cells are enclosed in a small space using a plate with small wells (96-well plate), micropores or the like, a method wherein cells are aggregated by centrifugation for a short time using a small centrifugal tube, and the like.

Any culture vessel can be used to form aggregates, as far as it allows a homogenous aggregate of stem cells to be formed by allowing "the cells to aggregate quickly"; those skilled in the art are able to determine the choice as appropriate. Such culture vessels include, for example, flasks, tissue culture flasks, dishes, Petri dishes, tissue culture dishes, multi-dishes, microplates, micro-well plates, micropores, multi-plates, multi-well plates, chamber slides, Petri dishes, tubes, trays, culturing bags, and roller bottles. For rapid aggregation of the cells, use of a culture vessel having a comparatively small culture space is preferable as mentioned above. From the viewpoint of forming homogenous aggregates, it is preferable that these culture vessels be non-cell-adhesive. Useful non-cell-adhesive culture vessels include culture vessels whose surfaces have not undergone an artificial treatment for improving the cell adhesiveness (e.g., coating treatment with an extracellular matrix and the like).

A culture vessel to be used for floating-culture is not particularly limited as long as floating-culture of cells is possible, and those same as the above-mentioned culture vessels can be used. When aggregates are subjected to floating-culture, the culture vessel is preferably non-cell-adhesive, like those mentioned above. As a culture vessel to be used for floating-culture, the one used for forming aggregates may be directly used.

The concentration of stem cells at the time of aggregate formation can be set as appropriate to allow aggregates of stem cells to be formed more homogenously and efficiently by those skilled in the art. However, high cell density (HCD) (also referred to as large cell-aggregation (LCA) condition) is preferably employed, so that the expression of endogenous growth factors in the aggregate will be increased, and as a result, differentiation into both a central nervous tissue and a non-neural head ectodermal tissue (particularly, a rostral hypothalamus tissue and a rostral head ectodermal tissue) will be induced simultaneously. While aggregate formation has been carried out by seeding cells at low cell concentrations in the prior art (e.g., non-patent document 5, patent document 3, etc.), with such low cell concentration, the expression of endogenous growth factors in the aggregate is less likely to increase and, unless stimulation with a exogenous BMP signal promoter (e.g., BMP4) is applied, simultaneous differentiation into both a central nervous tissue and a non-neural head ectodermal tissue (particularly, a rostral hypothalamus tissue and a rostral head ectodermal tissue) is hardly induced.

The above-mentioned "endogenous growth factor" refers to BMPs (Bone Morphogenetic proteins), particularly, BMP2, BMP4, or both BMP2 and BMP4. The "increased" expression of endogenous growth factors in the aggregate means an increase in the expression of endogenous growth factors at a time point on day 7 or thereafter from the start of the culture at a high cell concentration, as compared to that when the aggregate is formed at a low cell concentration (for example, 3000 cells/aggregate), and refers to an increase of at least not less than 1.8-fold, preferably not less than 1.9-fold, more preferably not less than 2.0-fold. When the expression of endogenous growth factors is too high, formation of a central m nervous tissue and a non-neural head ectodermal tissue which induce formation of placode for pituitary gland and sensory organ, particularly a rostral hypothalamus tissue and a rostral head ectodermal tissue (in the case of hypophysis placode) may be conversely suppressed. Therefore, an increase in the expression of the endogenous growth factor is generally not more than 5.0-fold, preferably not more than 4.0-fold, more preferably not more than 3.5-fold.

While the expression of endogenous growth factors may be measured by either the mRNA level or protein level, it is preferably measured at the mRNA level. Quantification of protein and mRNA may be performed using methods known in the art. Quantification of mRNA is preferably performed by quantitative PCR (for example, real-time PCR). In one embodiment, the expression level of endogenous growth factors refers to the expression level of one of BMP4 and BMP2.

In one embodiment, at a time point on day 7 or thereafter from the start of the culture at a high cell concentration, the expression of either BMP2 or BMP4 in the aggregate formed at a high cell concentration is at least not less than 1.8-fold, preferably not less than 1.9-fold, more preferably not less than 2.0-fold, as compared to that when the aggregate is formed at a low cell concentration (for example, 3000 cells/aggregate). In addition, at the same time point, the expression of either BMP2 or BMP4 in the aggregate is generally not more than 5.0-fold, preferably not more than 4.0-fold, more preferably not more than 3.5-fold, as compared to those of low cell concentration.

In one embodiment, at a time point on day 7 or thereafter from the start of the culture at a high cell concentration, the expression of each of BMP2 and BMP4 in the aggregate formed at a high cell concentration is at least not less than 1.8-fold, preferably not less than 1.9-fold, more preferably not less than 2.0-fold, as compared to that when the aggregate is formed at a low cell concentration (for example, 3000 cells/aggregate). In addition, at the same time point, the expression of each of BMP2 and BMP4 in the aggregate is generally not more than 5.0-fold, preferably not more than 4.0-fold, more preferably not more than 3.5-fold, as compared to those of low cell concentration.

In one embodiment, to induce simultaneous differentiation into both a central nervous tissue and a non-neural head ectodermal tissue (particularly a rostral hypothalamus tissue and a rostral head ectodermal tissue which is a sheet-like continuous epithelium) in an aggregate, it is important to form the aggregate at a cell concentration that enables to achieve an "increase" in the expression of the endogenous growth factors (i.e., BMP2 and/or BMP4) as mentioned above in the aggregate (high cell density (HCD) or large cell-aggregation (LCA) conditions). In particular, when stimulation with exogenous BMP signal promoter (e.g., BMP4) is absent, it is preferable to form the aggregate at a cell concentration that achieves an "increase" in the expression of the endogenous growth factors (i.e., BMP2 and/or BMP4) in the aggregate (high cell density (HCD) or large cell-aggregation (LCA) conditions).

Where necessary, to induce differentiation into both a central nervous tissue and a non-neural head ectodermal tissue (particularly a rostral hypothalamus tissue and a rostral head ectodermal tissue) in an aggregate, an exogenous signal promoter of a protein belonging to the BMP subfamily in the TGF-β superfamily may be added to the following serum-free medium, in addition to the above-mentioned conditions, at a concentration that does not cause suppression of neural differentiation or for a period that does not cause suppression of neural differentiation. Here, the proteins belonging to the BMP subfamily refer to those classified as BMPs (BMP2/4 group (BMP2, BMP4), OP-1 group (BMP5, BMP6, BMP7, BMP8a, BMP8b), BMP9 group (BMP9, BMP10), GDF5 group (GDF5, GDF6, GDF7)) and GDFs (Growth and Differentiation Factors). BMP2 and/or BMP4 are/is particularly preferable, and BMP4 is most preferable.

The promoter (e.g., BMP4) of a signal of a protein belonging to the exogenous BMP subfamily (e.g., BMPs) may be comprised in the serum-free medium from the time of formation of the aggregate, or may be added to the serum-free medium after the lapse of a given time from the start of floating-culture. The period from the start of floating-culture of aggregate after the start of floating-culture to the addition of the above-mentioned signal promoter is generally within 240 hours, preferably within 96 hours, more preferably within 72 hours.

In one embodiment, from the viewpoint of not suppressing the neural differentiation, a signal promoter (e.g., BMP2 and/or BMP4) of a protein belonging to the BMP subfamily (e.g., BMPs) is added to a serum-free medium after a lapse of a predetermined period of time from the start of the floating-culture. That is, the above-mentioned signal promoter is added to a serum-free medium after a lapse of 48 hours, at the earliest, from the start of the floating-culture.

The concentration of the signal promoter of a protein belonging to the exogenous BMP subfamily (e.g., BMPs) is, for example, within the range of 0.01-10 nM when BMP2 or BMP4 is used.

Moreover, to promote differentiation into a central nervous tissue and a non-neural head ectodermal tissue (particularly a rostral hypothalamus tissue and a rostral head ectodermal tissue which is a sheet-like continuous epithelium) in an aggregate, the serum-free medium may comprise a Shh signal promoter.

The Shh signal promoter is not particularly limited, as far as it is capable of enhancing the signal transduction mediated by Shh. Shh signal promoters include, for example, proteins belonging to the Hedgehog family (e.g., Shh, Shh-N), Shh receptors, Shh receptor agonists (e.g., Purmorphamine, SAG); most preferably SAG.

Since SAG has a several-fold stronger activity than Shh and can be used up to high concentrations relatively inexpensively, it can induce a strong activity of hedgehog signaling (Danjo et al, JNS, 2010).

The Shh signal promoter may be comprised in a serum-free medium from the time of formation of the aggregate, or may be added to a serum-free medium after the lapse of a given time from the start of the floating-culture of the aggregate. The period from the start of floating-culture of aggregate after the start of floating-culture to the addition of the Shh signal promoter is generally within 192 hours, preferably within 168 hours, more preferably within 144 hours.

The concentration of the Shh signal promoter to be used only needs to be a concentration that can promote differentiation into both a central nervous tissue and a non-neural head ectodermal tissue (particularly a rostral hypothalamus tissue and a rostral head ectodermal tissue which is a sheet-like continuous epithelium) in an aggregate. Such concentration when using SAG is, for example, generally about 10-2000 nM, preferably about 50-1000 nM, most preferably about 100-400 nM, in the following serum-free medium.

In a preferable embodiment, to induce differentiation into both a central nervous tissue and a non-neural head ectodermal tissue (particularly a rostral hypothalamus tissue and a rostral head ectodermal tissue) in an aggregate, a signal promoter (preferably BMP2 and/or BMP4) of a protein belonging to the exogenous BMP subfamily (e.g., BMPs), and a Shh signal promoter (preferably, SAG) are added to a serum-free medium used for the formation of aggregate and/or floating-culture. In this case, the signal promoter of a protein belonging to the exogenous BMP subfamily (e.g., BMPs) may be comprised in the serum-free medium from the time of formation of the aggregate, or may be added to the serum-free medium after the lapse of a given time from the start of floating-culture. The period from the start of floating-culture to the addition of the above-mentioned signal promoter is generally within 240 hours, preferably within 96 hours, more preferably within 72 hours. The signal promoter is preferably added to a serum-free medium after a lapse of 48 hours, at the earliest, from the start of the floating-culture, so that the neural differentiation will not be suppressed. The Shh signal promoter may be comprised in a serum-free medium from the time of formation of the aggregate, or may be added to a serum-free medium after the lapse of a given time from the start of the floating-culture of the aggregate. The period from the start of floating-culture to the addition of the Shh signal promoter is generally within 192 hours, preferably within 168 hours. The concentration range of each factor is as mentioned above.

When stem cells of mouse are used, those skilled in the art can set the stem cell concentration at the time of aggregate formation as appropriate to form aggregates of stem cells more homogenously and efficiently. The concentration of the stem cells on aggregate formation is preferably started from a high cell concentration, so that aggregates of stem cells comprising $5 \times 10^3$-$1.5 \times 10^4$ stem cells (preferably $8 \times 10^3$-$1.5 \times 10^4$ stem cells) per one aggregate will be formed, which will increase the expression of endogenous growth factors in the aggregate, and enable induction of simultaneous differentiation into both a central nervous tissue and a non-neural head ectodermal tissue, for example, both a rostral hypothalamus tissue and a rostral head ectodermal tissue. For example, when a 96 well microwell plate is used, a liquid prepared to comprise about $4.5 \times 10^3$-$5 \times 10^4$ cells, preferably about $5 \times 10^3$-$1.5 \times 10^4$ cells, most preferably about $8 \times 10^3$-$1.5 \times 10^4$ cells, per well (150 μl) is added, and the plate is stood to allow formation of aggregates. Using a culture vessel having a sufficiently small culture space, one aggregate can be formed per well. In this case, the same number as the number of stem cells comprised in one aggregate formed ($5\times10^3$-$1.5\times10^4$ cells, preferably $8\times10^3$-$1.5\times10^4$ cells), or somewhat greater number of stem cells, are added to one well, and cultivated, whereby desired aggregates of stem cells comprising $5\times10^3$-$1.5\times10^4$ stem cells (preferably $8\times10^3$-$1.5\times10^4$ stem cells) per one aggregate can be formed. Those of ordinary skill in the art can easily and appropriately adjust the number of cells to be added to one well to form aggregates of stem cells comprising $5\times10^3$-$1.5\times10^4$ stem cells (preferably $8\times10^3$-$1.5\times10^4$ stem cells) per one aggregate, in consideration of the conditions such as size, shape of well, volume of medium and the like.

Even when stem cells of human are used, those skilled in the art can set the stem cell concentration at the time of aggregate formation as appropriate to form aggregates of stem cells more homogenously and efficiently. The concentration of the stem cells on aggregate formation is preferably started from a high cell concentration, so that the expression of endogenous growth factors in the aggregate will be increased, and simultaneous differentiation into both a central nervous tissue and a non-neural head ectodermal tissue (particularly both a rostral hypothalamus tissue and a rostral head ectodermal tissue) can be induced. In case of human, to induce simultaneous differentiation into both a central nervous tissue and a non-neural head ectodermal tissue (particularly a rostral hypothalamus tissue and a rostral head ectodermal tissue which is a sheet-like continuous epithelium) in an aggregate, it may be necessary to increase the cell number than the above-mentioned concentration for mouse. For example, the high cell concentration for human is preferably a concentration that can form aggregates of stem cells comprising about $0.9\times10^4$-$3\times10^4$ stem cells per one aggregate. For example, when a 96 well microwell plate is used, the cells are prepared to be about $0.9\times10^4$-$3\times10^4$ per well (150 μl) or somewhat greater number of cells, and desired aggregates of stem cells comprising $0.9\times10^4$-$3\times10^4$ stem cells per one aggregate can be formed. On the other hand, as mentioned above, when a signal promoter (e.g., BMP2 and/or BMP4) of a protein belonging to the BMP subfamily (e.g., BMPs) is added to a serum-free medium, the cell concentration does not always need to be high, and a concentration that forms aggregates of stem cells comprising $0.3\times10^4$-$3\times10^4$ stem cells per one aggregate is preferable. Those of ordinary skill in the art can appropriately adjust the appropriate number of cells in consideration of the conditions such as size, shape of well, volume of medium and the like.

Even when stem cells other than those from mouse or human is used, the number of stem cells per one aggregate can be appropriately adjusted according to the animal species from which the stem cells derive, so that the expression of endogenous growth factors in the aggregate will be increased, and simultaneous differentiation into both a central nervous tissue and a non-neural head ectodermal tissue, particularly both a rostral hypothalamus tissue and a rostral head ectodermal tissue which is a sheet-like continuous epithelium can be induced.

Other culturing conditions such as culturing temperature and $CO_2$ concentration at the time of aggregate formation can be set as appropriate. The culturing temperature is not particularly limited, and is, for example, about 30 to 40° C., preferably about 37° C. The $CO_2$ concentration is, for example, about 1 to 10%, preferably about 5%.

Although the time to the formation of the aggregate can be determined as appropriate according to the stem cell used, as far as cells are allowed to aggregate quickly, it is desirable that the formation be performed as soon as possible to ensure the formation of homogenous aggregates. Such formation of aggregates has been performed over about 2 days (see, for example, Watanabe, K. et al., Nature Neurosci. 8, 288-296, Schuldiner M, Benvenisty N. Factors controlling human embryonic stem cell differentiation. Methods Enzymol. 2003; 365:446-461); by contrast, this time has been shortened to enable efficient differentiation induction of desired tissues, cells and the like. In case of mouse embryonic stem cells, for example, it is desirable that the aggregates be formed preferably within 12 hours, more preferably within 6 hours. Meanwhile, in case of human embryonic stem cells, it is desirable that the aggregates be formed preferably within 24 hours, more preferably within 12 hours. If this time is exceeded, homogenous aggregates of stem cells may not be formed, which in turn can cause a remarkable reduction in differentiation efficiency in the subsequent step. This time to aggregate formation can be adjusted as appropriate by choosing a tool for cell aggregation, centrifugal conditions and the like by those skilled in the art.

Those skilled in the art are able to evaluate the "homogenous" formation of aggregates of stem cells and the formation of an epithelium-like structure in each cell type that forms the aggregates, on the basis of the size of the m aggregate mass and the number of cells therein, macroscopic morphology, microscopic morphology and homogeneity thereof as analyzed by histological staining, the expression of differentiation and un-differentiation markers and homogeneity thereof, the regulation of the expression of differentiation markers and synchronicity thereof, reproducibility of differentiation efficiency among aggregates, and the like.

Specifically, homogenous aggregates of stem cells can be formed by, for example, a method comprising culturing embryonic stem cells for maintenance, suspending the dispersion-treated (e.g., trypsin/EDTA treated) embryonic stem cells in an appropriate medium (changed to the below-mentioned medium according to the object tissue or cell), and floating the cells in 150 μL of the above-described medium at preferably $1\times10^3$-$5\times10^4$ cells, more preferably $3\times10^3$-$3\times10^4$ cells per well in a non-cell-adhesive U-bottom 96-well culture plate to form an aggregate rapidly.

Other culture conditions in the floating-culture of aggregates such as the culture temperature, $CO_2$ concentration and the like can also be set as appropriate and, for example, the same conditions as those described above as the culture conditions for aggregate formation and the like can be mentioned. While the time for this step is not particularly limited, it is generally 48 hours or more.

A medium used for forming aggregates and a medium used for floating-culturing may be the same or different, and a medium used for forming aggregates may be directly used for floating-culturing.

The medium to be used for aggregate formation/floating-culturing can be prepared using a medium used for culturing animal cells as a basal medium. The basal medium is not particularly limited as long as it can be used for culture of animal cells and may be BME medium, BGJb medium, CMRL 1066 medium, Glasgow MEM medium, Improved MEM Zinc Option medium, IMDM medium, Medium 199 medium, Eagle MEM medium, αMEM medium, DMEM medium, ham medium, RPMI 1640 medium, Fischer's medium, a mixed medium thereof and the like.

The serum-free medium used for aggregate formation/floating-culturing means a medium free of an unadjusted or unpurified serum. In the present invention, those mentioned above can be recited.

Generally, serum-free medium is often added with several growth factors (Wnt, TGFβ, BMP, retinoic acid, FGF, lipid-rich albumin and the like) as an alternative to the serum. However, these growth factors all inhibit the differentiation of pituitary precursor tissue. In addition, insulin which is most frequently added to the serum-free medium strongly inhibits the differentiation of pituitary precursor tissue. It is considered that the inhibition is caused by the activation of intracellular enzyme (phosphoenzyme) Akt which is a downstream signal of insulin (non-patent document 5 and patent document 3).

Therefore, the above-mentioned serum-free medium, particularly a medium used for floating-culturing (to be also referred to as "differentiation medium" in the present specification) is preferably a serum-free medium substantially free of growth factors (Nodal signal promoter, Wnt signal promoter, FGF signal promoter, BMP signal promoter, retinoic acid and the like, preferably any growth factor not limited thereto) and insulins.

The above-mentioned serum-free medium can be, for example, one comprising a serum substitute. The serum substitute can, for example, be one comprising as appropriate an albumin, transferrin, fatty acids, insulin, collagen precursor, trace elements, 2-mercaptoethanol or 3'-thiolglycerol, or their equivalents and the like. Such a serum substitute can be prepared by, for example, a method described in WO98/30679. To facilitate easier implementation of a method of the present invention, commercially available serum substitutes can be utilized. Examples of such commercially available serum substitutes include Knockout Serum Replacement (KSR), Chemically-defined Lipid Concentrated (produced by Gibco Company) and Glutamax (produced by Gibco Company).

When these serum substitutes comprise growth factors and insulins, inhibitors against the growth factors and insulins are preferably added to the medium as described below. However, it is preferable to not use a serum substitute comprising growth factors and insulins. The serum substitute is preferably a chemically-defined product evidently free of growth factors and insulins.

However, in the case of pluripotent stem cells of primates including humans, floating-culture without insulins may lead to low viability, as described below. In such case, addition of insulins to the medium is also preferable.

In addition, the serum-free medium used in the method of the present invention can comprise fatty acids or lipids, amino acids (e.g., non-essential amino acids), vitamins, growth factors, anti-oxidants, 2-mercaptoethanol, pyruvic acid, buffering agents, inorganic salts and the like as necessary. However, it is most preferable to not comprise growth factors, as mentioned above.

The "serum-free medium that substantially does not comprise growth factors and insulins" refers to a serum-free medium that does not at all comprise growth factors and insulins, or a serum-free medium that comprises growth factors and/or insulins in an amount that does not adversely influence the selective differentiation of pituitary precursor tissue and pituitary hormone-producing cells. Such a serum-free medium can be prepared by, for example, non-addition of growth factors and insulins as medium components, or by a treatment to remove these factors from the medium comprising these factors which are growth factors and insulins.

Alternatively, the serum-free medium that substantially does not comprise growth factors and insulins can be a serum-free medium wherein the growth factors and insulins have been substantially inactivated; this medium refers to a serum-free medium wherein by adding a growth factor signal inhibitor and/or an insulin signal inhibitor to a serum-free medium comprising growth factor and insulin, the activities of the growth factors and insulins have been lost to an extent that does not adversely influence the selective differentiation of pituitary precursor tissue and pituitary hormone-producing cells.

Referring to "a medium that substantially free of growth factors" as mentioned herein, "a growth factor" means an optionally chosen factor that is generally added as a serum substitute in cell culture using a serum-free medium, and that has the action of inhibiting/suppressing the selective differentiation of pituitary precursor tissue and pituitary hormone-producing cells from an ES cell. Examples of the "growth factors" include, but are not limited to, Nodal signal promoters, Wnt signal promoters, FGF signal promoters, BMP signal promoters, retinoic acid and the like. "A medium that substantially does not comprise a growth factor" is preferably a medium that substantially does not comprise all of Nodal signal promoters, Wnt signal promoters, FGF signal promoters, BMP signal promoters and retinoic acid. Lipid-rich albumin is also included in "growth factor", the medium used in the present invention is preferably a medium that does not comprise lipid-rich albumin.

As used herein, the "insulins" means a compound that promotes insulin signals. An insulin signal promoter is not particularly limited, as far as it acts to promote the transduction of signals of insulin, and the promoter may act on any stage of the insulin signaling pathway (factors that act on the upstream or downstream of insulin, insulin agonists, similar substances and the like).

Insulins include insulin and insulin analogues. Insulin analogues refers to an optionally chosen substance having an insulin-like action (herein, refers to an action to inhibit/suppress the selective differentiation into pituitary precursor tissue and pituitary hormone-producing cells, from pluripotent stem cells); examples include IGF-I and the like.

For the treatment to remove growth factors and insulins from the medium comprising the growth factors and insulins to obtain the above-described serum-free medium, for example, antibodies against the above-described growth factors (e.g., Nodal signal promoters, Wnt signal promoters, FGF signal promoters, BMP signal promoters, retinoic acid, lipid-rich albumin and the like) and insulins can be used. Inactivation of growth factors and insulins can be performed by the addition of growth factor signal inhibitor and insulin signal inhibitor. These inhibitors can be optionally chosen substances that inhibit the upstream or downstream of the signal transduction pathway by the growth factors or insulins; examples include antibodies against growth factors/insulins, soluble receptors of growth factors/insulins, antibodies against growth factor/insulin receptors, growth factors/insulins antagonists and the like. These substances are added to the medium in amounts suitable for obtaining the desired effect (selective differentiation into pituitary precursor tissue and pituitary hormone-producing cells).

However, as mentioned above, the above-mentioned serum-free medium may comprise an exogenous signal promoter of BMP2 and/or BMP4 (e.g., BMP2 and/or BMP4), at a concentration not causing suppression of neural differentiation, so that simultaneous differentiation into both a central nervous tissue and a non-neural head ectodermal tissue, particularly both a rostral hypothalamus tissue and a rostral head ectodermal tissue which is a sheet-like continuous epithelium can be induced. When BMP2 and/or BMP4 are/is added, it is preferably added to a concentration of 0.01-10 nM so that neural differentiation will not be easily suppressed.

While substances usable for the removal treatment of growth factors/insulins specifically recited above are explained in the following, it is needless to say that selection of substances usable for the removal treatment of other growth factors/insulins, adjustment of the amount of use thereof and the like are within the range of general techniques of those of ordinary skill in the art.

The Nodal signal inhibitor is not particularly limited, as far as it is capable of suppressing the signal transduction mediated by Nodal. Nodal signal inhibitors include, for example, SB431542 (Sigma), Lefty-A, Lefty-B, Lefty-1, Lefty-2, soluble Nodal receptors, Nodal antibodies, and Nodal receptor inhibitors; in particular, SB431542 (4-(5-benzo[1,3]dioxol-5-yl-4-pyridin-2-yl-1H-imidazol-2-yl)-benzamide) is preferable.

The Wnt signal inhibitor is not particularly limited, as far as it is capable of suppressing the signal transduction mediated by Wnt. Wnt signal inhibitors include, for example, Dkk1, Cerberus protein, Wnt receptor inhibitors, soluble Wnt receptors, Wnt antibodies, casein kinase inhibitors, and dominant negative Wnt protein; in particular, Dkk1 is preferable.

The FGF signal inhibitor is not particularly limited, as far as it is capable of suppressing the signal transduction mediated by FGF. FGF signal inhibitors include, for example, anti-FGF antibodies, soluble FGF receptors, and FGF receptor inhibitors (e.g., Su5402).

The BMP signal inhibitor is not particularly limited, as far as it is capable of suppressing the signal transduction mediated by BMP. BMP signal inhibitors include, for example, BMPRFc (R&D), anti-BMP antibodies, soluble BMP receptors, and BMP receptor inhibitors; in particular, BMPRFc is preferable.

The retinoic acid (RA) inhibitor is not particularly limited, as far as it is capable of suppressing the signal transduction mediated by RA. RA inhibitors include, for example, anti-RA antibodies, soluble RA receptors, and RA receptor inhibitors.

The concentration of each of the above-described signal inhibitors used for floating-culturing can be a concentration that allows selective differentiation into hypothalamic neuron progenitor cells to be achieved. For example, for SB431542, the concentration is about 0.1 to 100 nM, preferably about 5 to 30 nM. For Dkk1, the concentration is about 10 to 1000 ng/ml, preferably about 100 to 1000 ng/ml. For BMPRFc, the concentration is about 0.1 to 10 µg/ml, preferably about 0.5 to 3 µg/ml.

Each of the signal inhibitors described above is most preferably added to the medium already at the start of culturing the pluripotent stem cells.

The intracellular signaling of insulin is involved by roughly two pathways (MAPK pathway and PI3K-Akt pathway); insulin signal inhibitors that can be used in the floating-culture of the present invention include inhibitors of PI3K, which is a downstream factor in the insulin signaling pathway, and inhibitors of Akt, which is a further downstream factor. PI3K inhibitors that can be used in the present invention include LY294002 (2-(4-morpholinyl)-8-phenyl-1(4H)-benzopyran-4-one hydrochloride) (Cayman Chemical), Wortmannin (FERMENTEK) and the like; LY294002 is preferable. Akt inhibitors that can be used in the present invention include Akt inhibitors I to X (Calbiochem) and the like; Akt inhibitor VIII (1,3-Dihydro-1-(1-((4-(6-phenyl-1H-imidazo[4,5-g]quinoxalin-7-yl)phenyl)methyl)-4-piperidinyl)-2H-benzimidazol-2-one) is preferable.

As far as insulin signals are inhibited, and the selective differentiation of pituitary precursor tissue or pituitary hormone-producing cells is achieved, in the floating-culture, any one inhibitor selected from among the above-described PI3K inhibitors and Akt inhibitors may be used alone, or a PI3K inhibitor and an Akt inhibitor may be used in combination. Two kinds or more can be selected from among the respective inhibitors and used in combination.

The concentration of the PI3K inhibitor/Akt inhibitor used in the floating-culture can be a concentration that allows the selective differentiation into pituitary precursor tissue or pituitary hormone-producing cells to be achieved. For example, for LY294002, the concentration is about 0.5 to 30 µM, preferably about 2 to 10 µM. For Akt inhibitor VIII, the concentration is about 0.1 to 10 µM, preferably about 0.5 to 5 µM.

The differentiation medium used in a preferred embodiment of the present invention is a chemically defined medium that comprises neither the above-described growth factors nor insulin (growth factor-free CDM; referred to as gfCDM). Specifically, as the differentiation medium, Iscove's Modified Dulbecco's Medium (IMDM)/Hams F12 1:1 (Invitrogen) added with 1×chemically-defined lipid concentrate (Invitrogen), monothioglycerol (450 µM; Sigma) and bovine serum albumin (recrystallization purified product with >99% purity; Sigma) is used (Wataya et al., PNAS. 105(33), 11796-11801). This gfCDM medium is a modification of a previously reported CDM medium (Mol. Cell. Biol. 15:141-151 (1995)).

To suppress the action of endogenous growth factors/insulins, a growth factor inhibitor/insulin inhibitor may be further added to the gfCDM medium or another medium.

In another preferred embodiment, the differentiation medium used the present invention is a serum-free medium that comprises at least one inhibitor selected from the group consisting of PI3K inhibitors and Akt inhibitors and insulins, and that substantially does not comprise the above-described growth factors other than insulin. For example, particularly, when floating-culture is performed using an insulin-free medium in differentiation induction of primate pluripotent stem cells, there are some cases in which the cells die and are unlikely to proliferate. To avoid such cell death, it is preferable that insulin be added to facilitate cell proliferation, and an insulin signal inhibitor that antagonizes the differentiation induction inhibitory effect of insulin (e.g., PI3K inhibitor/Akt inhibitor) be added at the same time. In this case, the concentration of the insulin comprised in the differentiation medium is a concentration that allows the proliferation of pluripotent stem cells to be promoted. For example, the concentration is normally about 0.02 to 40 µg/ml, preferably about 0.1 to 10 µg/ml, for insulin. The ranges of concentrations of the PI3K inhibitor and the Akt inhibitor are as described above.

Although the PI3K inhibitor/Akt inhibitor is added to the medium most preferably already at the start of culturing the pluripotent stem cells, the inhibitor should be added to the differentiation medium at a time at least until day 6 of cultivation (preferably at least until day 2 of cultivation) for the differentiation of rodent (e.g., mouse) pluripotent cells, and at a time at least until day 24 of cultivation (preferably added at least until day 9 of cultivation) for the differentiation of primate (e.g., human) pluripotent cells.

To suppress cell death during dispersion floating-culture, it is preferable that in addition to the addition of insulin, a ROCK inhibitor (Y-27632 ((+)-(R)-trans-4-(1-aminoethyl)-

N-(4-pyridyl)cyclohexanecarboxamide dihydrochloride); Watanabe et al., Nature Biotechnology, 25, 681-686, 2007) be added from the start of cultivation. The concentration of the ROCK inhibitor used for floating-culturing is a concentration that allows cell death during dispersion floating-culture to be suppressed. For example, for Y-27632, this concentration is normally about 0.1 to 200 μM, preferably about 2 to 50 μM.

(4) Induction of Further Differentiation

In the present invention, since aggregates are formed under the conditions of high cell concentration of pluripotent stem cells as mentioned above, expression of endogenous growth factors increases in the aggregate of stem cells, and simultaneous differentiation into a rostral hypothalamus tissue and a rostral head ectodermal tissue which is a sheet-like continuous epithelium is induced. In such aggregates, to promote differentiation induction into Lim3-positive cells, to promote differentiation induction into Rathke's pouch-like tissue (pituitary precursor tissue), or to further differentiate the obtained pituitary precursor tissue into hypophysis hormone-producing cells, floating-culture can be performed using the medium described below.

Schematic drawings of in vivo pituitary development are shown in FIG. 1a, and a schematic drawing of the development of various pituitary hormone-producing cells is shown in FIG. 3a.

(A) Differentiation Induction of Lim3-Positive Cells and Pituitary Precursor Tissues In the present invention, since aggregates are formed under the conditions of high cell concentration of pluripotent stem cells, expression of endogenous growth factors increases in the aggregate of stem cells, and differentiation into a rostral hypothalamus tissue and a rostral head ectodermal tissue which is a sheet-like continuous epithelium is induced in one aggregate. To promote differentiation of the cells comprised in the aggregate into Lim3-positive cells, and to promote differentiation into pituitary precursor tissue (Rathke's pouch), a serum-free medium to be used for floating-culturing may comprise a Shh signal promoter.

The concentration of the Shh signal promoter to be used only needs to be a concentration that can promote differentiation into Lim3-positive cells. Such concentration when using SAG is, for example, generally about 10-2000 nM, preferably about 50-1000 nM, most preferably about 100-400 nM, in a serum-free medium (preferably gfCDM).

The timing of adding a Shh signal promoter to a serum-free medium is not particularly limited so long as it can promote the induction of Lim3 positive cells in aggregates, and it may not be added to the medium when floating-culturing is started. However, as the time up to the addition of Shh signal promoter becomes longer, the expression level of Lim3 mRNA induced in the aggregates decreases (see FIG. 1i), and therefore, it is preferable to add the Shh signal promoter from the start of the floating-culture. For example, a Shh signal promoter is preferably added to a medium at the time of the start of floating-culture to three days after floating-culture, more preferably at the time of the start of floating-culture to two days after floating-culture, still more preferably at the time of the start of floating-culture to one day after floating-culture, most preferably at the time of the start of floating-culture.

While the period of floating-culture in a serum-free medium comprising a Shh signal promoter is not particularly limited as long as it is sufficient for inducing Lim3-positive cells, for example, it is generally about 7-14 days for mouse aggregates and generally about 10-30 days for human aggregates.

The concentration of Shh signal promoter in the medium may be changed as necessary during the culture. For example, aggregates may be subjected to the floating-culture in a serum-free medium comprising a Shh signal promoter, until Lim3-positive cells are induced in the aggregates, and once the Lim3-positive cells are induced, the floating-culture can be continued in a serum-free medium free of a Shh signal promoter. In one embodiment, when SAG is used, differentiation induction of pituitary precursor tissues can be promoted by using a medium comprising SAG at a concentration of 100 nM to 400 nM from the start of the floating-culture up to the induction of the Lim3-positive cells (e.g., up to day 10 of culture), and thereafter using a medium free of SAG. In one embodiment, when differentiation of pituitary precursor tissues into various pituitary hormone-producing cells is induced, a medium comprising 400 nM SAG is used from the start of the floating-culture to day 7 of culture, thereafter a medium comprising 100 nM SAG is used up to day 10 of culture and thereafter a medium free of SAG can be used, and in another embodiment, a medium comprising 400 nM SAG is used from the start of the floating-culture to day 10 of culture, and thereafter, half of the medium is exchanged and culture may be continued up to day 8. As long as differentiation induction into pituitary precursor tissue is promoted, the conditions are not limited to these. After the induction of Lim3-positive cells, the floating-culture may be continued in a serum-free medium comprising a Shh signal promoter to induce differentiation into pituitary hormone-producing cells. Preferably, the aggregate is subjected to floating-culture in a serum-free medium comprising a Shh signal promoter until Lim3-positive cells are induced in the aggregate, and once the Lim3-positive cells are induced, the floating-culture is continued in a serum-free medium free of a Shh signal promoter, whereby the Lim3-positive cells in the aggregate form a Lim3-positive epithelial pouch vesicle (i.e., pituitary precursor tissue).

In one embodiment, aggregates of stem cells comprising $8 \times 10^3$-$1.5 \times 10^4$ stem cells per one aggregate (in the case of mouse stem cells) or aggregates of stem cells comprising $9 \times 10^3$-$3 \times 10^4$ stem cells per one aggregate (in the case of human stem cells) are formed in a serum-free medium, and the formed aggregates are subjected to floating-culture in a serum-free medium comprising a Shh signal promoter, whereby aggregates comprising both a hypothalamus tissue and a non-neural head ectoderm are formed. Lim3-positive cells are induced in the aggregates, as a result of which, aggregates comprising both a hypothalamus tissue and a non-neural head ectoderm, and Lim3-positive cells can be obtained.

In one embodiment, an aggregate comprising both a hypothalamus tissue and a non-neural head ectoderm (preferably, further comprising Lim3-positive cells) is further subjected to floating-culture in a serum-free medium substantially free of a Shh signal promoter, whereby a Lim3-positive epithelial pouch vesicle is formed in the aggregate and a hypophysis precursor tissue can be obtained.

(B) Promotion of Differentiation Induction of Pituitary Precursor Tissue

To promote differentiation induction into pituitary precursor tissue in the differentiation induction into pituitary precursor tissue, namely, to increase the number of Lim3-positive epithelial pouch vesicles formed in the aggregates or increase the expression level of Lim3 mRNA, a medium comprising an FGF signal promoter can also be used after floating-culture in the above-mentioned serum-free medium comprising a Shh signal promoter.

The FGF signal promoter is not particularly limited as long as it can enhance signaling mediated by FGF. Preferable examples of the FGF signal promoter include FGFs (e.g., FGF1-23), FGF agonist, and FGF receptor agonist peptide. Preferable FGF signal promoter is FGF8 and/or FGF10.

While the concentration of the FGF signal promoter to be used only needs to be a concentration that can increase the number of lim3 expressing cells formed or can increase the expression level of Lim3 mRNA. In the case of FGF8 or FGF10, such concentration is, for example, about 2-1000 ng/ml, preferably about 20-400 ng/ml, most preferably about 200 ng/ml, in a serum-free medium, preferably gfCDM.

While the FGF signal promoter may be added to the medium at any time point of floating-culture of aggregates, it is preferably added to the above-mentioned medium free of a Shh signal promoter, which is used after the culture in a serum-free medium comprising a Shh signal promoter. For example, aggregates may be subjected to floating-culture in a serum-free medium comprising a Shh signal promoter, until Lim3-positive cells are induced in the aggregates, and once the Lim3-positive cells are induced, the floating-culture can be continued in a serum-free medium free of a Shh signal promoter and comprising a FGF signal promoter (preferably FGF8 or FGF10). In one embodiment, a SAG-comprising medium (e.g., medium comprising 100 nM to 400 nM SAG) is used from the start of the floating-culture until induction of Lim3-positive cells (e.g., up to day 10 of culture), thereafter a medium free of SAG and comprising a FGF signal promoter (preferably FGF8 or FGF10) is used. In this case, the FGF signal promoter (preferably FGF8 or FGF10) may be added to the medium at any time point after induction of Lim3-positive cells (e.g., day 10 of culture and thereafter), the FGF signal promoter (preferably FGF8 or FGF10) is maintained in the above-mentioned concentration range preferably for 3 days preferably in day 10 of culture-day 18 of culture, more preferably day 10 of culture-day 13 of culture.

(C) Differentiation Induction into ACTH-Producing Cells

To induce differentiation of the formed pituitary precursor tissue into ACTH-producing cells after formation of pituitary precursor tissue, the pituitary precursor tissue can be further subjected to floating-culture in a serum-free medium comprising a Notch signal inhibitor. The "ACTH-producing cells" used in the present specification refers to pituitary ACTH-producing cells, and does not include ACTH$^+$ neuron.

The Notch signal inhibitor is not particularly limited, as far as it is capable of suppressing the signal transduction mediated by Notch. Notch signal inhibitors include, for example, DAPT, DBZ, MDL28170 and the like; in particular, DAPT is preferable.

The concentration of the Notch signal inhibitor to be used may be a concentration that can achieve differentiation induction into ACTH-producing cells. In the case of DAPT, such concentration is, for example, about 0.1-1000 μM, preferably about 0.5-500 μM, more preferably about 1-100 μM, most preferably about 10 μM, in a serum-free medium, preferably gfCDM medium.

A serum-free medium comprising a Notch signal inhibitor is used after the formation of pituitary precursor tissue by the above-mentioned floating-culture. Such medium may be used at any time point after formation of the pituitary precursor tissue. A serum-free medium comprising a Notch signal promoter preferably does not comprise a Shh signal promoter. For example, as mentioned above, when a SAG-comprising medium is used from the start of the culture until formation of Lim3-positive, epithelial pouch vesicles (e.g., up to day 10 of culture) (e.g., a medium comprising 400 nM SAG from the start of the culture to day 7, and a medium comprising 100 nM SAG for day 7-day 10), and thereafter a medium free of SAG is used, a Notch signal inhibitor (e.g., DAPT) may be added at any time point after formation of Lim3-positive epithelial pouch vesicles in aggregates (i.e., after formation of pituitary precursor tissue). Preferably, pituitary precursor tissue is subjected to floating-culture in a serum-free medium (preferably gfCDM medium) comprising a Notch signal inhibitor (e.g., DAPT) in the above-mentioned concentration range, for about 3 days, preferably, about 1 day, in day 10 of floating culture-day 30 of culture, more preferably day 14 of culture-day 22 of culture, still more preferably day 18 of culture-day 22 of culture, most preferably days 18-19 of culture or days 20-21 of culture. In one embodiment, after culture in a SAG-comprising medium and on day 18 of culture, 10 μm DAPT is added to the medium and half of the medium is exchanged on day 19 and culture is performed for 1 day.

(D) Differentiation Induction into Pituitary Hormone-Producing Cells Other than ACTH-Producing Cells To induce differentiation of the formed pituitary s precursor tissue into pituitary hormone-producing cells other than ACTH-producing cells (GH-producing cells, PRL-producing cells, LH-producing cells, FSH-producing cells and TSH-producing cells), the pituitary precursor tissue can be further subjected to floating-culture in the following medium after formation of the pituitary precursor tissue.

(i) Differentiation Induction into GH-Producing Cells

For differentiation induction into GH-producing cells, a serum-free medium comprising glucocorticoids can be used. Examples of the glucocorticoids include hydrocortisone (also called cortisol), corticosterone, synthetic compounds having the same biological activity as theirs (dexamethasone and the like) and the like. To enhance the efficiency of differentiation induction into GH-producing cells, the serum-free medium preferably further comprises insulins. As examples of insulins, those recited in the present specification and the like can be mentioned.

For example, the medium that can be used for inducing differentiation into GH-producing cells in the present invention is a serum-free medium, preferably gfCDM medium, comprising about 2-about 2000 ng/ml, preferably about 20-1000 ng/ml, most preferably about 200 ng/ml, of hydrocortisone, or about 0.1—about 100 ng/ml, preferably about 1-50 ng/ml, most preferably 10 ng/ml, of dexamethasone, and about 0.2-30 nM, preferably about 0.5-10 nM, most preferably about 1 nM, of insulins.

The above-mentioned medium is preferably used after a treatment with a Shh signal inhibitor. For example, when a SAG-comprising medium is used from the start of the culture to formation of Lim3-positive, epithelial pouch vesicles (e.g., up to day 10 of culture) (e.g., a medium comprising 400 nM SAG from the start of the culture to day 7, and a medium comprising 100 nM SAG for days 7-10), and thereafter a medium free of SAG is used, glucocorticoid and insulins may be added at any time point after formation of Lim3-positive epithelial pouch vesicles in the aggregates (i.e., after formation of pituitary precursor tissue). Preferably, the pituitary precursor tissue is subjected to floating-culture in a serum-free medium comprising glucocorticoid and insulins for days 10-40 from the start of floating-culture, preferably days 15-35 from the start of floating-culture, preferably days 20-33 from the start of floating-culture, most preferably days 20-30 from the start of floating-culture.

(ii) Differentiation Induction into PRL-Producing Cells

For differentiation induction into PRL-producing cells, a serum-free medium comprising an estrogen can be used. Examples of the estrogen include estradiol, estrone, estriol, estetrol, synthetic compounds having the same biological activity as theirs and the like. To enhance the efficiency of differentiation induction into PRL-producing cells, the serum-free medium preferably further comprises insulins. As examples of insulins, those recited in the present specification and the like can be mentioned.

For example, the medium that can be used for inducing differentiation into PRL-producing cells in the present invention is a serum-free medium, preferably gfCDM medium, comprising about 5-about 500 ng/ml, preferably about 10-200 ng/ml, most preferably about 50 ng/ml, of estradiol, and about 0.2-30 nM, preferably about 0.5-10 nM, most preferably about 1 nM, of insulins.

The above-mentioned medium is preferably used after a treatment with a Shh signal inhibitor. For example, when a SAG-comprising medium is used from the start of the culture to formation of Lim3-positive, epithelial pouch vesicles (e.g., up to day 10 of culture) (e.g., a medium comprising 400 nM SAG from the start of the culture to day 7, and a medium comprising 100 nM SAG for days 7-10), and thereafter a medium free of SAG is used, estradiol and insulins may be added at any time point after formation of Lim3-positive epithelial pouch vesicles in the aggregates (i.e., after formation of pituitary precursor tissue). Preferably, the pituitary precursor tissue is subjected to floating-culture in a serum-free medium comprising estradiol and insulins for days 10-40 from the start of floating-culture, preferably days 14-34 from the start of culture, preferably days 20-33 from the start of floating-culture, most preferably days 20-30 from the start of floating-culture.

(iii) Differentiation Induction into LH-Producing Cells, FSH-Producing Cells and TSH-Producing Cells For example, differentiation into LH-producing cells, FSH-producing cells and TSH-producing cells can be induced by floating-culture of the pituitary precursor tissue in a serum-free medium comprising a culture supernatant obtained by cultivating stromal cells in a serum-free medium (preferably gfCDM) (conditioned medium of stromal cells) (for 4-10 days).

Here, the "conditioned medium of stromal cells" refers to a medium comprising a stromal cell-derived soluble factor, which can be prepared by recovering the supernatant of a medium after culture of stromal cells.

Examples of the stromal cells include PA6 cells, MEF cells, OP9 cells and the like, with particular preference given to PA6 cells.

The above-mentioned serum-free medium is preferably used after the treatment with a Shh signal inhibitor. For example, when a SAG-comprising medium is used from the start of the culture to formation of Lim3-positive, epithelial pouch vesicles (e.g., up to day 10 of culture) (e.g., a medium comprising 400 nM SAG from the start of the culture to day 7, and a medium comprising 100 nM SAG for days 7-10), and thereafter a medium free of SAG is used, an conditioned medium of stromal cells may be added at any time point after formation of Lim3-positive epithelial pouch vesicles in the aggregates (i.e., after formation of pituitary precursor tissue). Preferably, the pituitary precursor tissue is subjected to floating-culture in a serum-free medium comprising an acclimation medium of stromal cells for days 10-30 from the start of culture, preferably days 10-20 from the start of culture, most preferably days 10-15 from the start of culture.

When differentiation into cells, which are differentiated via Pitx1-positive intermediate progenitor cells (i.e., GH-producing cells, PRL-producing cells and TSH-producing cells), is induced from among the pituitary hormone-producing cells of the above-mentioned (i)-(iii), the ratio of each hormone-producing cell can be further increased by using a serum-free medium comprising each component to be added for differentiation induction and further comprising a Wnt signal promoter (see FIG. 3a). For example, under the above-mentioned culture conditions, a medium comprising a Wnt signal promoter can be used preferably for at least 2 days during days 10-30 from the start of culture, preferably days 12-24 from the start of culture, most preferably days 16-18 from the start of culture. When differentiation into GH-producing cells or PRL-producing cells is induced, a Wnt signal promoter may be added to a serum-free medium before or simultaneously with the addition of glucocorticoid or estrogen (and insulin as necessary). It is preferably added to a serum-free medium before the addition of glucocorticoid or estrogen (and insulin as necessary).

The Wnt signal promoter is not particularly limited, as far as it is capable of enhancing the signaling mediated by Wnt. Wnt signal promoters include, for example, proteins belonging to the Wnt family (e.g., Wnt1-16), GSK3β inhibitors, Wnt receptors, the Li$^+$ ion and the like; in particular, GSK3β inhibitors are preferable.

Examples of the GSK3β inhibitor include, but are not limited to, GSK-3β Inhibitors I, VI, VII, VIII, XI, XII, CHIR 99021, Valproic Acid, TDZD-8, SB-216763, BIO (6-bromoindirubin-3'-oxime) and the like.

The concentration of Wnt signal promoter is not limited as long as it can increase the ratio of pituitary hormone-producing cells as compared to that without a Wnt signal promoter. For example, when BIO is used, the concentration thereof is generally about 20-2000 nM, preferably about 50-500 nM, most preferably about 250 nM.

In one embodiment, a serum-free medium comprising 250 nM BIO is used from day 16 from the start of the culture, half of the medium is exchanged on day 18, and the culture is performed for 2 days.

(5) Promotion of Pituitary Hormone Secretion

Each pituitary hormone-producing cell obtained by the method described above is treated with a substance that promotes the production and secretion of each pituitary hormone, whereby the production and secretion of pituitary hormones can be stimulated. The substance that promotes the production and secretion of each hypophysis hormone (also referred to as hormone secretagogue) may be a substance that directly acts on each pituitary hormone-producing cell or a substance that acts indirectly in vivo, for example, after transplantation and the like.

Specifically, production and secretion of ACTH is promoted by CRH and the like, production and secretion of GH is promoted by GHRH and the like, production and secretion of TSH is promoted by TRH and the like, production and secretion of PRL is promoted by PRF (specific examples are mentioned above), TRH and the like, and production and secretion of FSH and LH is promoted by GnRH and the like. These promoting substances to be used may be isolated from natural sources, or may be synthesized by recombination and the like.

The culture conditions for secreting pituitary hormone from pituitary hormone-producing cells can be appropriately set as long as they do not adversely affect the survival and proliferation of pituitary hormone-producing cells, and promote production and secretion of pituitary hormones. For example, eight aggregates comprising the pituitary hormone-producing cells are placed in 500 µl of HBSS solution and, after pre-incubation for 10 min, each stimulator at an appropriate final concentration is added at 37° C., and the cells are incubated for 10 min more at 37° C.

When the differentiated ACTH-producing cells are stimulated with CRH, the production and secretion of ACTH is generally induced markedly by using not less than about 10 ng/ml of CRH. CRH is preferably used at a concentration of about 10-10000 ng/ml, more preferably about 100-10000 ng/ml, more preferably about 1000-10000 ng/ml.

When the production and secretion of GH is stimulated with GHRH, a preferable concentration range is 100 nM-500 nM, when the production and secretion of TSH is stimulated with TRH, a preferable concentration range is 1 nM-5 nM, when the production and secretion of PRL is stimulated with PRF (e.g., prolactin release peptide mentioned above), a preferable concentration range is 2 nM-10 nM, when the production and secretion of FSH is stimulated with GnRH, a preferable concentration range is 1 nM-20 nM, and when the production and secretion of LH is stimulated with GnRH, a preferable concentration range is 1 nM-20 nM.

Pituitary hormones produced from pituitary hormone-producing cells can be isolated and purified from the culture. Pituitary hormones can be isolated and purified from, for example, a culture supernatant by a method known per se for the isolation and purification of peptide and protein (known methods such as gel filtration and ion exchange chromatography).

(6) Cell Culture Products and Use as Pharmaceuticals

The present invention also provides a cell culture product obtained by a method of the present invention. The cell culture product of the present invention can be, for example, a floating aggregate comprising stem cells or cells differentiated from the stem cells, cells prepared by dispersion-treating (e.g., trypsin/EDTA treatment) the floating aggregate, cells obtained by culturing the dispersion-treated cells and the like. The present invention also provides the pituitary precursor tissue or the pituitary hormone-producing cells isolated and purified from the cell culture product to an extent that allows the tissue or cells to be administered to a subject.

"A culture product" refers to a resulting product obtained by culturing cells, and include cells, medium, and, in some cases, components secreted from cells and the like. "Isolation" means removing components other than the desired tissues or cells (cells, proteins, medium and the like).

The pituitary precursor tissue or pituitary hormone-producing cells obtained by the method of the present invention can be used as a therapeutic drug for the following diseases, for supplementing pituitary tissue or pituitary hormone-producing cells when the pituitary tissue or cells are damaged due to other causes, and the like.

Alternatively, pituitary hormone produced by the pituitary hormone-producing cells obtained by the method of the present invention can be used as a therapeutic drug for the following diseases, for supplementing an appropriate pituitary hormone in deficiency of pituitary hormone secretion caused by damage to any pituitary tissue or respective pituitary hormone-producing cells (hormone replacement therapy) and the like.

Examples of the diseases treatable by the pituitary precursor tissue or pituitary hormone-producing cells obtained by the method of the present invention include hypoadrenocorticism, growth hormone deficiency dwarfism, adult-onset GH deficiency, pituitary dwarfism, cretinism, infertility, panhypopituitarism (including empty sella syndrome, pituitary apoplexy, postoperative pituitary damage), partial hypopituitarism, isolated anterior pituitaryhormone deficiency (specifically, isolated ACTH deficiency, isolated growth hormone deficiency, isolated TSH deficiency, isolated prolactin deficiency, isolated gonadotropic hormone deficiency) and the like.

When pituitary precursor tissue or pituitary hormone-producing cells obtained by the method of the present invention is used as a therapeutic drug for the diseases based on the disorders of pituitary tissue or pituitary hormone-producing cells, it is preferable that the cells be transplanted to the subject after increasing the purity of the pituitary precursor tissue or pituitary hormone-producing cells.

Any method of increasing cell purity can be used, as far as it is a method of cell separation and purification in public knowledge; such methods include, for example, a method using a flow cytometer (see, for example, Antibodies—A Laboratory Manual, Cold Spring Harbor Laboratory (1988), Monoclonal Antibodies: principles and practice, Third Edition, Acad. Press (1993), Int. Immunol., 10, 275 (1998)), the panning method (see, for example, Monoclonal Antibodies: principles and practice, Third Edition, Acad. Press (1993), Antibody Engineering, A Practical Approach, IRL Press at Oxford University Press (1996), J. Immunol., 141, 2797 (1988)), and cell fractionation based on differences of sucrose density (see, for example, Soshiki Baiyou no Gijyutsu (3rd edition)).

The method for increasing purity of cells of the present invention comprises a step for culturing pituitary precursor tissue or pituitary hormone-producing cells obtained by inducing the differentiation of the above-described stem cells, in a medium comprising an anticancer agent. Thereby, undifferentiated cells can be removed, making it possible to obtain differentiated cells of higher purity, which are more suitable for pharmaceutical use. Hence, by a treatment with an anticancer agent, cells other than desired differentiated cells, for example, undifferentiated cells, can be removed.

Here, the anticancer agent is exemplified by mitomycin C, 5-fluorouracil, Adriamycin, Ara-C, methotrexate and the like. These anticancer agents are preferably used at concentrations that are more cytotoxic to undifferentiated cells than to induced differentiated cells. Specifically, cultivation with these anticancer agents may be performed in accordance with the above-described procedures of cultivation to determine optimum concentrations; for example, a method, wherein cells are cultured in a $CO_2$ incubator aerated with 5% carbon dioxide at 37° C. for several hours, preferably for 2 hours, using a medium comprising these anticancer agents at concentrations one-hundredth to one time the concentrations for live bodies specified in the Japanese Pharmacopoeia, is mentioned.

Any medium that allows cultivation of the differentiation-induced pituitary precursor tissue or pituitary hormone-producing cells can be used here. Specifically, the aforementioned media and the like can be mentioned.

In transplantation therapy, graft rejection due to the difference in the histocompatibility antigen is often problematic, which problem, however, can be solved by using a stem cell having the nucleus of a somatic cell transplanted thereto, or a stem cell having a modified gene on the chromosome thereof.

By inducing differentiation using a stem cell having the nucleus of a somatic cell transplanted thereto, pituitary precursor tissue or pituitary hormone-producing cells of the individual which is the donor of the somatic cell can be obtained. Tissues or cells of such an individual are not only effective in transplantation therapy as they are, but also useful as a diagnostic material for determining whether or not an existing drug is effective on the individual. Furthermore, by culturing the induced differentiated tissues or cells for a long period, it is possible to determine their susceptibility to oxidative stress and senescence; by comparing their functions or life spans with those of cells from other individuals, it is possible to evaluate the individual risks of contracting the above-mentioned diseases; these evaluation data are useful in providing an effective prophylactic method for diseases diagnosed as developing at high incidences in the future.

A subject to be transplanted with the pituitary precursor tissue or pituitary hormone-producing cells is a warm-blooded animal, preferably a mammal, more preferably an animal of the same species as the animal from which the original stem cells derive. Examples of the mammal include rodents such as mouse, rat, hamster, guinea pig and the like, experiment animals such as rabbit and the like, domestic animals such as swine, bovine, goat, horse, sheep and the like, pets such as dog, cat and the like, and primates such as human, monkey, orangutan, chimpanzee and the like. When the transplantation aims at a treatment of a disease, the subject is preferably a human patient.

The induced pituitary precursor tissue or pituitary hormone-producing cells differentiated from stem cells by the method of the present invention can be transplanted to anterior pituitary or a region corresponding thereto by a method known per se When production and secretion of pituitary hormone is desired, the pituitary precursor tissue or hypophysis hormone-producing cells can be transplanted to any part of the subject as long as the production and secretion of the hormone can be induced. For example, the pituitary precursor tissue or pituitary hormone-producing cells can be transplanted to pituitary of the subject or in the vicinity thereof or, when pituitary has been removed, the site where pituitary should be present (i.e., pituitary fossa), or in the vicinity of the target organ on which the secreted pituitary hormone acts and the like (e.g., under renal capsule for ACTH-producing cells, etc.). As shown in the Examples, ACTH-producing cells can fulfill the ACTH-producing function even when transplanted ectopically.

The production and secretion of pituitary hormone in the subject after implantation may be stimulated by administering a hormone secretagogue as described above to the subject, or may be naturally stimulated by such endogenous substances. It can be appropriately selected depending on the object of transplantation and the condition of the subject and the like.

To be specific, as a method for transplanting pituitary hormone-producing cells to a subject mouse, a method comprising injecting about 1-1000, preferably about 5-500, more preferably about 10-50, cell aggregates comprising said cells obtained by the differentiation induction method of the present invention under renal capsule with a Hamilton syringe and the like can be mentioned. The method is not limited thereto as long as engraftment of the transplanted cells can be ensured. For transplantation as a pituitary precursor tissue (Rathke's pouch-like tissue), a method comprising isolating Rathke's pouch-like tissue from the cell aggregates, and injecting same under renal capsule with the Hamilton syringe and the like can be mentioned.

When the subject is a human, a method comprising transplanting the cell aggregates to subcutaneous tissues or in the vicinity of pituitary can be mentioned, though not limited thereto.

The engraftment of the transplanted tissue or cells can be confirmed by histochemical staining of pituitary hormone produced and secreted by the cells or other appropriate marker gene products with a fluorescence antibody after a lapse of sufficient time after transplantation (e.g., 7 days post-transplantation), and the like.

Alternatively, it can also be confirmed by measuring the production of other hormone (e.g., glucocorticoid (e.g., corticosterone) for ACTH) showing production and secretion promoted by said pituitary hormone, for example, blood concentration. Said other hormone and the like whose production and secretion is promoted by pituitary hormone, are as mentioned above.

Particularly, the effect of transplantation of the ACTH-producing cells can also be evaluated by the improvement of spontaneous locomotor activity of the recipient. For example, the spontaneously locomotor activity of mouse is evaluated by the distance of spontaneous movement in a cage per day and spontaneous rotation number of running wheel in a cage per day. The distance of movement of mouse in a cage can be measured by an analysis system using an IR sensor of MDC-W02 (BrainScienceIdea, Osaka) and the like, and the rotation number of the running wheel can be measured using ENV-044 (MedAssociates, Georgia) and the like. These measurements are performed as separate experiments by setting each apparatus in a cage (home cage) where the mouse to be measured is ordinarily reared. In this way, the amount of spontaneous locomotor activity can be measured under a low stress.

The effect of the transplantation of ACTH-producing cells can also be evaluated by the survival rate of the recipients. For example, the survival rate after transplantation of ACTH-producing cells can be analyzed by the Kaplan-Mayer method.

In addition, since the aggregates and pituitary precursor tissue obtained by the method of the present invention well reproduce the micro-environment during pituitary development in vivo, it is also useful as a research material relating to the development of pituitary, induction of pituitary hormone-producing cells and the like.

Furthermore, the method of the present invention is extremely useful since it can provide a "tissue material" useful in the field of regenerative medicine, for discovery of the aforementioned medicaments and the like drug, toxicity test and the like.

(7) Screening Method

The present invention provides screening method of a test substance, comprising using the cell culture product of the present invention or the culture product of the present invention. Particularly, since the culture product of the present invention constructs a pituitary precursor tissue extremely similar to the initial process of histogenesis of pituitary precursor tissue in a live body, and comprises cells extremely similar to the pituitary hormone-producing cells in a live body, it can be applied to a screening for therapeutic drugs for diseases based on disorders of pituitary tissue or various pituitary hormone-producing cells, screening for therapeutic drugs for cell injuries due to other causes, or toxicity studies thereof, and development of a new therapeutic method for diseases of nervous systems and the like.

Here, "a test substance" is exemplified by substances whose efficacy as therapeutic drugs for the above-mentioned diseases is to be determined and substances that are therapeutic drugs for other diseases whose influences (e.g., toxicity) on pituitary tissue or various pituitary hormone-producing cells must be determined. The substance may be any one of low-molecular compounds, high-molecular compounds, proteins, genes (DNA, RNA and the like), viruses and the like. Such substances can be chosen as appropriate by those skilled in the art.

The present invention is hereinafter described more specifically by means of the following Examples, which, however, are for illustrative purposes only and never limit the scope of the invention.

EXAMPLES

Example 1: Simultaneous Induction of In-Vitro Differentiation Into Prosencephalon Tissue and Non-Neural Head Ectoderm by Serum-Free Floating-Culture of ES Cell Aggregates (Method)

Mouse ES cell aggregates were cultured for 7 days by the SFEBq/gfCDM method (Wataya et al, 2008, PNAS vol. 105, pp. 11796-11801) which is a method for selective-differentiation into prosencephalon, particularly hypothalamus tissue. To be specific, mouse ES cells dispersed into single-cells by a trypsin treatment were plated by 3000, 8000, 10000 or 15000 cells per a U-bottom well of 96 well plate with a low cell-adhesive coating to form aggregates. As the medium, a chemically synthesized medium gfCDM (Wataya et al, 2008, PNAS vol. 105, pp. 11796-11801) was used. Detection was performed using Rx::GFP (GFP knocked into Rx gene locus) as a marker of hypothalamus tissue, and Pitx1 antibody as a non-neural head ectoderm marker.

(Results)

Figure 6:
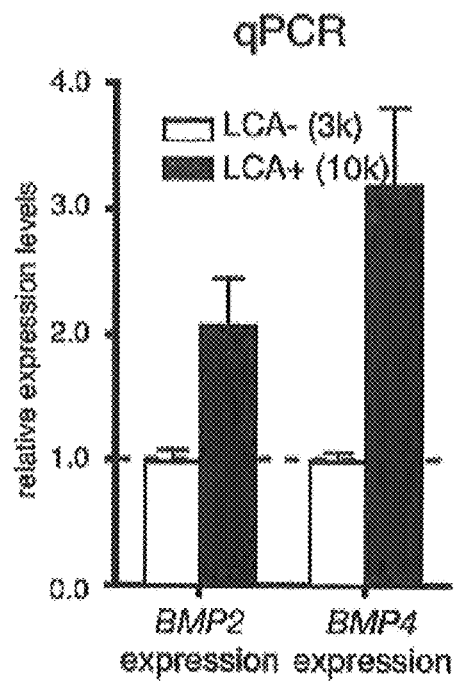
FIG. 6 shows the expression of BMP2 and BMP4 in gfCDM/SFEBq cultures started at 3000 cells/aggregate (LCA−) or 10000 cells/aggregate (LCA+).

The ES cell floating aggregates cultured by the SFEBq/gfCDM method for 7 days comprised, under all culture conditions, a hypothalamus marker Rx::GFP positive, neural marker N-cadherin and Sox1 positive hypothalamus tissue. In a culture forming aggregates of 8000-15000 cells per well, Pitx1-positive sheet-like continuous epithelial tissues were formed on the surface layer (further surface layer over Rx::GFP positive) in not less than 90% of the floating aggregates on day 5 of culture and thereafter (FIG. 1$f$). The aggregation from 3000 cells resulted in dispersion of a small number of Pitx1 cells, and a continuous large epithelium was not formed. In qPCR using another non-neural head ectoderm marker Pitx2, the aggregate from 10000 cells induced 4-fold expression of Pitx2 RNA as compared to the aggregate from 3000 cells, and the expression level of BMP2 and BMP4 mRNAs increased to about 2- to 3-fold (FIG. 6). It was found that the expression of Pitx2 increases by not only increasing the number of cells for forming aggregates but also adding BMP4 at a concentration of 0.5 nM to the medium (FIG. 1$d$).

Example 2: Serum-Free Floating-Culture of ES Cell Aggregates and Induction of In-Vitro Differentiation into Pituitary Precursor Tissue by Hedgehog Signal Treatment (Method)

Aggregates of mouse ES cells were formed from 10000 cells per aggregate by using the SFEBq/gfCDM method (Wataya et al, 2008, PNAS vol. 105, pp. 11796-11801), and subjected to the floating-culture as in Example 1. Immediately after the start of the differentiation culture, SAG (Danjo et al, JNS, 2011, vol. 31, pp. 1919-1933), a hedgehog agonist, was added at 100 or 400 nM, and the aggregates were cultured for a total of 10-13 days. Since SAG has a several-fold stronger activity than Shh, is comparatively cheap and can be used up to a high concentration, it can cause a strong hedgehog signaling activity (Danjo et al, JNS, 2011, vol. 31, pp. 1919-1933). The expression of Lim3, a marker of pituitary precursor tissue (Rathke's pouch), and the like was confirmed by PCR or cytochemical staining of frozen section by the fluorescence antibody method. The expression of Lim3 was also confirmed using Lim3::GFP knocked-in ES cells.

(Results)

In the group added with SAG at 100 or 400 nM, marked gene expression of Lim3 (15-fold that of undifferentiated ES cells, 7-fold that of SAG non-addition group) was confirmed by PCR on day 10 and later (also see FIGS. 1$j$, $k$). Since this induction of Lim3 was inhibited by SANT-1, an antagonist of hedgehog receptor, the action of SAG was found to be an effect via hedgehog signal.

Figure 2:
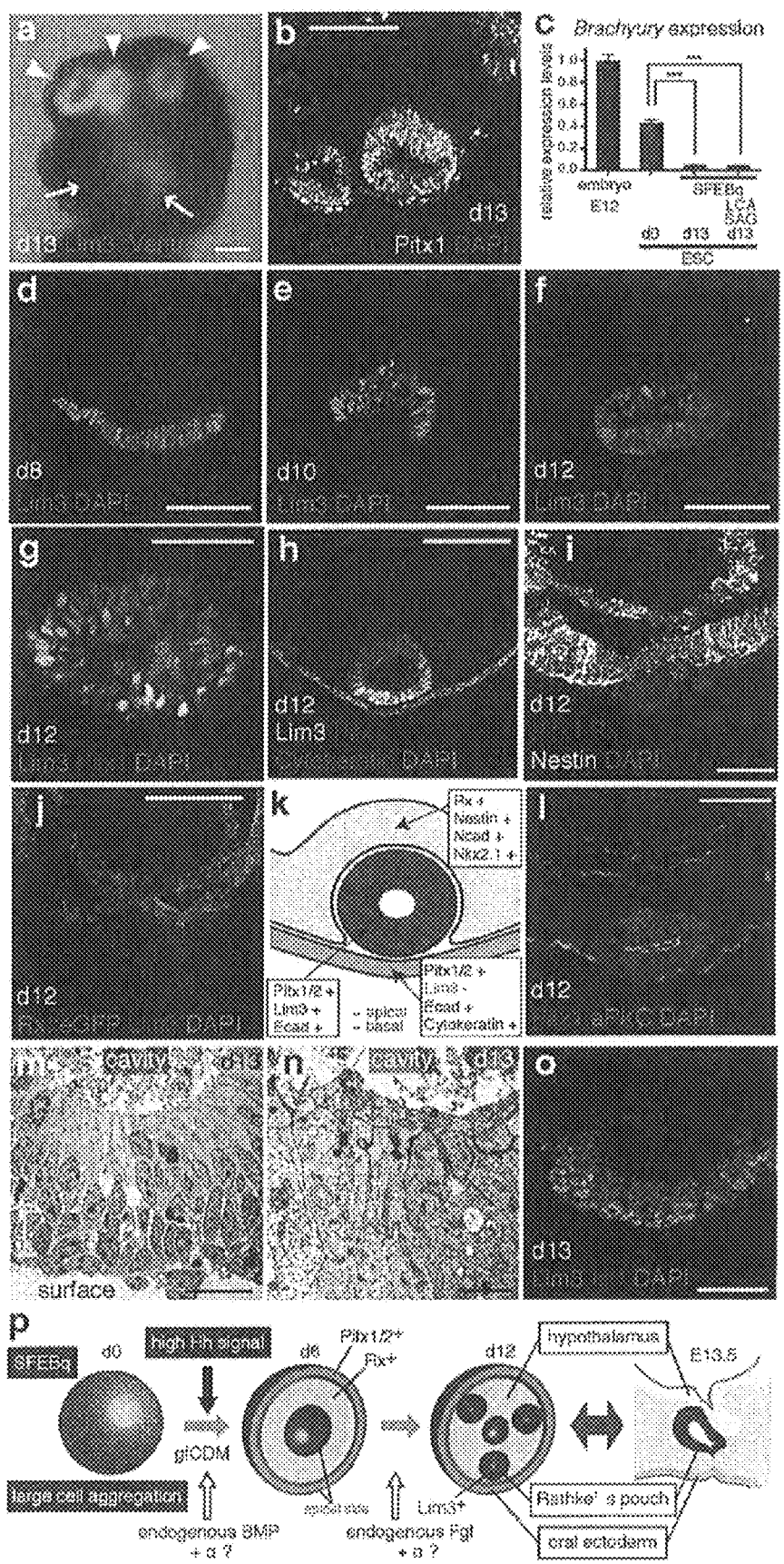
FIG. 2a shows clusters of lim3-positive cells in day-13 SAG-treated LCA aggregates.
FIG. 2b shows Lim3 positive cells in aggregates do not express a nerve cell marker Tuj1 (Lim3 (green), Tuj1 (red), Pitx1 (white)).
FIG. 2c shows little expression of mesoderm marker Brachyury in aggregates.
FIG. 2d-f shows aspects of formation of Rathke's pouch-like vesicles by lim3 positive cells in the aggregates (days 8-12).
FIG. 2g-j shows expression of marker genes in SAG-treated pouch vesicles and surrounding tissues (Pitx1 (red, g-i), lim3 (green, g; white, h; red, j), pancytokeratin (green, h), Rx (green, i, j)).
FIG. 2k shows a schematic figure showing marker gene expression in pouch vesicles and periphery thereof.
FIG. 2l shows in vivo expression of Pitx1 (red) and aPKC (green) (apical marker) in Rathke's pouch and surrounding tissues.
FIGS. 2m and 2n show electron microscopy images of pouch vesicles. Tall epithelial cells (m, apical, top), detached cells in the basal side (m, bracket), apical cilia (m, arrowheads), apical junction (m, arrow).
FIG. 2o shows Islet1 positive cells in the basal part of the pouch vesicles (Lim3 (green), Isl1 (red)).
FIG. 2p shows schematic of in vitro generation of the obtained Rathke's pouche-like vesicles. Scale bars, 100 μm (a-d, f, g); 50 μm (e, i, l); 20 μm (j); 2 μm (k).

The aggregates were further cultivated in gfCDM for 3 days (total 13 days). As a result, several (1-7) Lim3-positive epithelial pouch vesicles were formed in the aggregate in the SAG-addition group (FIG. 2$a$). The manner of formation of pouch vesicles is shown in FIGS. 2$d$-$f$ (d8-d10). The lim3 positive tissue first emerged as a thickened placode epithelium, then invaginated, and finally formed a hollow epithelial vesicle. These pouch vesicles were negative for Rx, Sox1 and Nestin and positive for Pitx1 and Pitx2 (FIGS. 2$g$-$j$), showed the same marker expressions as those of the pituitary precursor tissue, and began to express late Rathke's pouch marker Islet ½ in addition to Lim3 by day 13 (FIG. 2$o$). They had epithelial structures and polarity morphologically similar to those of the pituitary precursor tissue (FIGS. 2$m$, $n$). Moreover, like the pituitary precursor tissue (Rathke's pouch) in a live body, they were present in the vicinity of Rx-positive hypothalamus tissue, and were formed adjacent to Pitx1-positive and Lim3-negative non-neural head ectodermal tissue (FIGS. 2$h$, $k$). This suggests that the microenvironment for the development of a pituitary precursor tissue in the process of embryogenic development was imitated in this floating aggregate culture system of ES cells. Such Rathke's pouch-like tissue was scarcely formed in the culture started from an aggregate of 3000 cells.

gfCDM without SAG was used for culture during day 10-13. When FGF8 was added at 200 ng/ml during this period, the tissues expressing Lim3 increased by 30-50%.

Example 3: Production and DAPT Treatment of ACTH-Producing Cells from ES Cell-Derived Pituitary Precursor Tissue (Method)

Using the method of Example 2, mouse ES cells were differentiated into pituitary precursor tissue by a SAG treatment (400 nM for 7 days and 100 nM for 3 days, total 10 days). Furthermore, using gfCDM medium, the aggregates were cultured under 40% $O_2$ and 5% $CO_2$ for 12 days in total (total 22 days). Moreover, the aggregates were treated with Notch signal inhibitor, 10 μM DAPT, for one day during days 18-19 or days 20-21 of culture. The expression of Tbx19 and ACTH expressed in ACTH-producing cells was confirmed by cytochemical staining of frozen section by the fluorescence antibody method.

(Results)

Figure 3:
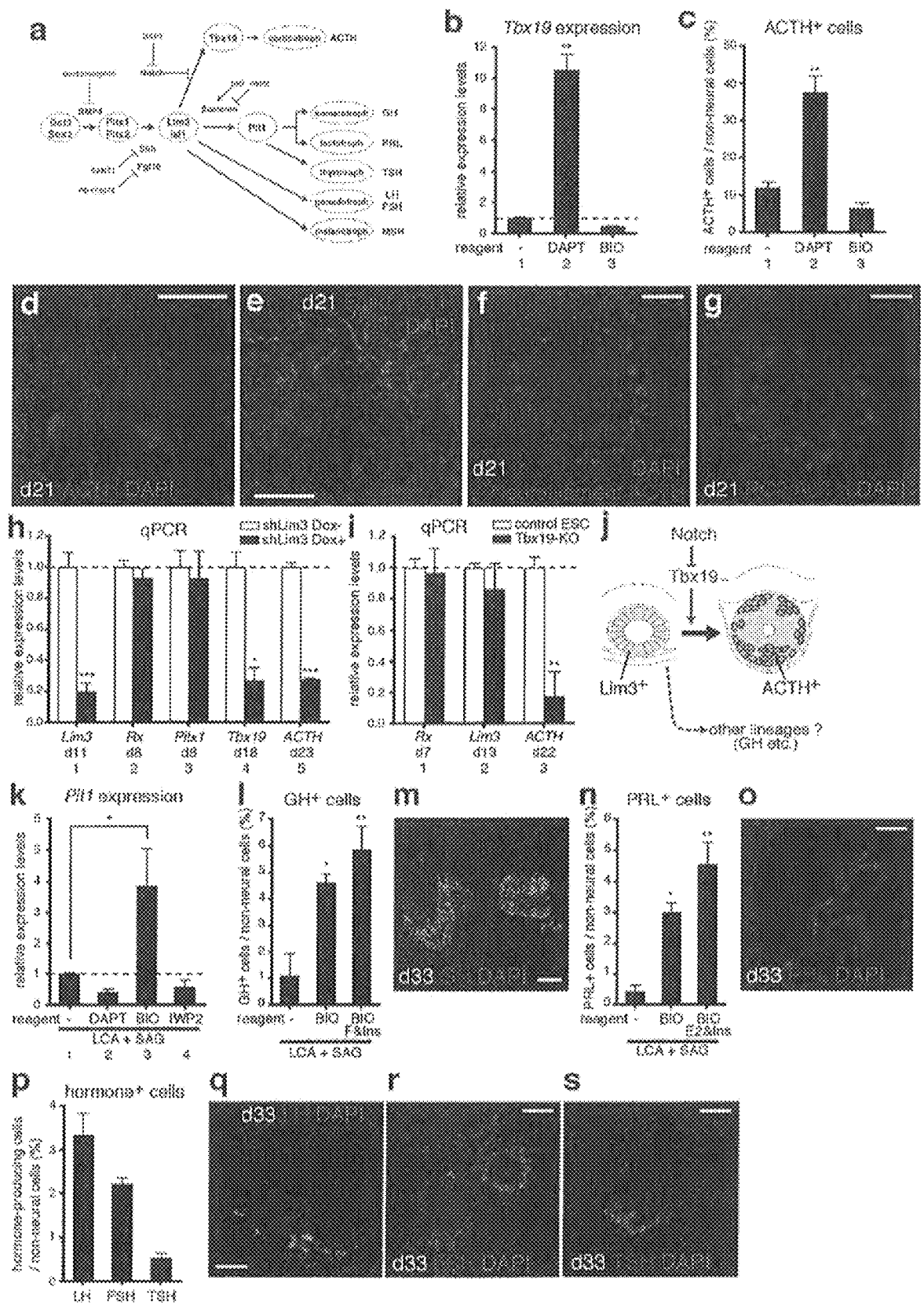
FIGS. 3 L and 3m show generation of GH$^+$ cells in LCA+ SAG aggregates (day 33) (hydrocortisone and insulin were added on days 20-30).

As a result of analysis by the fluorescence antibody method, the above-mentioned aggregate with DAPT treatment showed an enhanced expression of Tbx19 as compared to that without DAPT treatment (FIG. 3$b$), an increased percentage of ACTH-positive cells (FIG. 3$c$), and comprised assemblies of many Tbx19- and ACTH-highly positive cells (>30 cells or more) in plural sites. The aggregate without DAPT treatment merely showed a small number of dispersed Tbx19- and ACTH-positive cells. Since the ACTH-positive cells were negative for neural markers such as NSE, neurofilament and the like, they were considered other than brain ACTH$^+$ neuron (FIG. 3f), and did not express melanin-producing cell lineage marker PC2 (FIG. 3g). Furthermore, the ACTH$^+$ cells were E-cadherin negative as in vivo (FIG. 3e).

In vivo, during the pituitary development, Tbx19-negative precursor generates a Pitx1-positive intermediate precursor, and this precursor is thereafter differentiated into GH-producing cells, PRL-producing cells, and TSH-producing cells. The expression of Pitx1 was confirmed to find that the expression did not increase, or rather decreased, by the DAPT treatment and greatly increased by the BIO treatment. The expression of Pitx1 tended to decrease with Wnt-inhibitor IWP2 treatment (FIG. 3k).

Example 4: Production of Pituitary Hormone-Producing Cells Other than ACTH-Producing Cells from ES Cell-Derived Pituitary Precursor Tissue (Method)

Mouse ES cells were differentiated into pituitary precursor tissues by an SAG treatment (400 nM for 7 days and 100 nM for 3 days, total 10 days) using the method of Example 2. Furthermore, the aggregates were continuously floating-cultured under 40% $O_2$ and 5% $CO_2$. The medium used was gfCDM comprising corticosteroid (200 ng/ml hydrocortisone) and 1 nM insulin, gfCDM comprising estrogen (50 ng/ml estradiol) and 1 nM insulin, or culture supernatant (conditioned medium) of mouse feeder cell, PA6 cell, in gfCDM.

The expression of growth hormone (GH), prolactin (PRL), luteinizing hormone (LH), follicle-stimulating hormone (FSH), and thyroid-stimulating hormone (TSH) was confirmed by cytochemical staining of frozen section by the fluorescence antibody method.

(Results)

When cultured in gfCDM comprising corticosteroid (200 ng/ml hydrocortisone) and 1 nM insulin for 10 days from day 20 of culture, many GH-positive cells were confirmed in the aggregate (FIG. 3l, m). Furthermore, when BIO (250 nM) stimulating Wnt pathway was treated with a GSK3β inhibitor during days 16-18 of culture, the GH-positive cells further increased by 30-50%. When cultured in gfCDM comprising estrogen (50 ng/ml estradiol) and 1 nM insulin for 10 days from day 20 of culture, many Prolactin-positive cells were confirmed in the aggregate (FIGS. 3n, o). When cultured in the culture supernatant of PA6 cell in gfCDM for 15 days from day 10 of culture, many LH-positive cells and FSH-positive cells were confirmed, and a small number of TSH-positive cells were observed (LH-positive cells>FSH-positive cells>TSH-positive cells) (FIGS. 3p-s).

Example 5: In Vitro ACTH Secretion from ES Cell-Derived ACTH-Producing Cells by CRH (Method)

Mouse ES cells were differentiated into ACTH-producing cells by a SAG treatment and a DAPT treatment (total 22 days) using the method of Example 3. The aggregates were treated with CRH (corticotropin releasing factor) and ACTH secretion was quantified. To be specific, eight aggregates were placed in 500 μl of HESS solution and, after pre-incubation at 37° C. for 10 min, CRH was added at a final concentration of 10-10000 ng/ml, and the aggregates were incubated for 10 min. Then, the culture supernatant was recovered and measured by ELISA method (FIG. 4a).

(Results)

Figure 4:
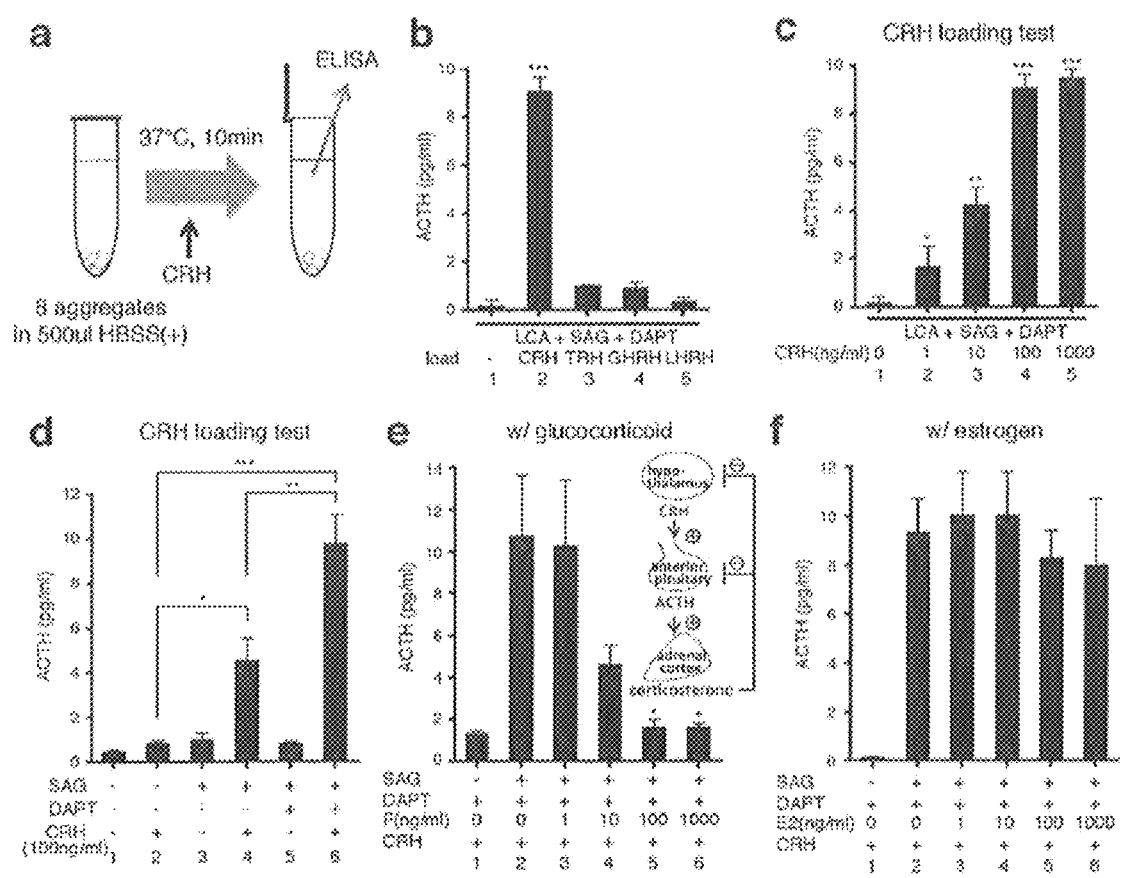
FIG. 4a shows schematic of CRH-loading test for ACTH secretion.
FIG. 4b shows enhancement of ACTH secretion by CRH-loading.
FIG. 4c shows enhancement of ACTH secretion by CRH-loading at various doses.
FIG. 4d shows influence of SAG, DAPT and CRH treatments on ACTH secretion from aggregates.
FIG. 4e shows that pretreatment with hydrocortisone (F), a negative feedback factor on ACTH secretion, suppressed the enhancement of ACTH secretion by CRH.
FIG. 4f shows that pretreatment with estradiol (E2) did not influence ACTH secretion.

In a group without addition of CRH, the ACTH concentration of the culture supernatant was not more than 0.2 pg/ml; however, 1.4 pg/ml ACTH was detected in 10 ng/ml CRH group, 4 pg/ml ACTH was detected in 100 ng/ml CRH group, and 8.5-9.5 pg/ml ACTH was detected in 1000 and 10000 ng/ml CRH groups (FIG. 4c). On the other hand, the aggregates without SAG treatment did not show a significant increase in the ACTH secretion even when added with 1000 ng/ml CRH, and the aggregates with a SAG treatment but without a DAPT treatment did not show much increase in the ACTH secretion even when added with CRH (FIG. 4d). The induction of ACTH secretion was CRH-specific, and was not observed even when other releasing hormones were added (FIG. 4b).

Furthermore, when a pre-treatment with hydrocortisone (100 ng/ml), which is known to suppress ACTH secretion from pituitary gland, was performed for 60 min, the ACTH secretion promoting effect of CRH was suppressed almost completely (FIG. 4e); however, a pre-treatment with estradiol did not affect the ACTH secretion (FIG. 4f).

Example 6: Secretion of ACTH and Corticotropin from ES Cell-Derived ACTH-Producing Cells by CRH In Vivo (Method)

Mouse ES cells were differentiated into ACTH-producing cells by a SAG treatment and a DAPT treatment using the method of Example 3, and the obtained cell aggregates were transplanted under renal capsule of hypophysectomized mice (FIG. 5a, right). Before transplantation, these mice were confirmed to have lost the ACTH secretion ability (reactivity to CRH) (FIGS. 5b, c).

To be specific, after culture for 22 days in total, the cell aggregates were injected under renal capsule of hypophysectomized mice with a Hamilton syringe. After 7 days from the transplantation and under a load of CRH intraperitoneal administration, the plasma was recovered and the ACTH and corticotropin (Corticosteron) concentrations were measured by ELISA method.

(Results)

Figure 5:
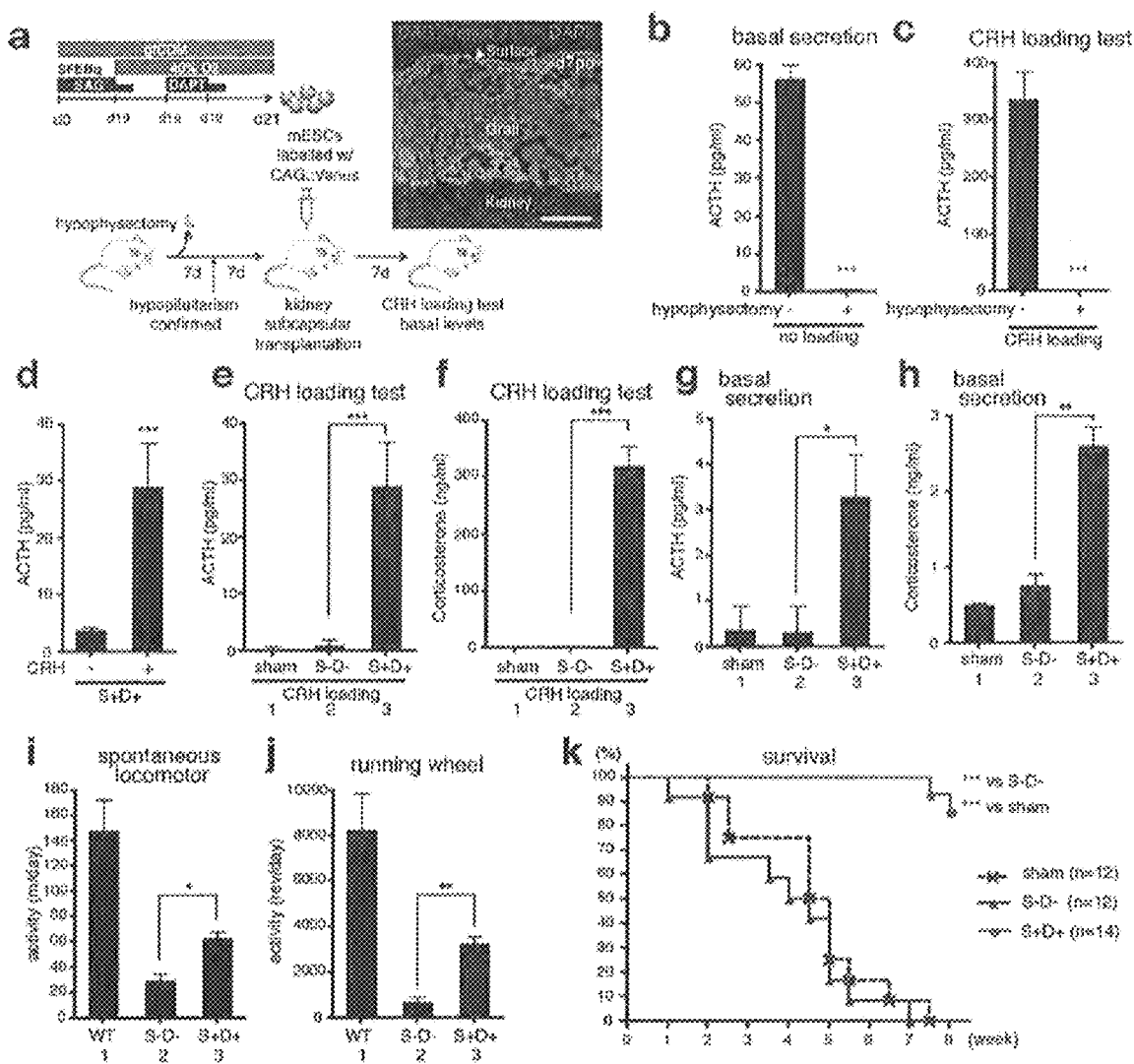
FIG. 5a shows design of transplantation experiment of aggregates into hypophysectomized mice and engraftment of aggregates (labeled with GFP) transplanted under the renal capsule on post-operative day 7 (red: ACTH$^+$ cells; blue: DAPI; scale bar, 100 μm).
FIGS. 5b and c shows that no-production of ACTH due to hypophysectomy (with (c) or without (b) CRH loading).
FIG. 5d shows ACTH levels in grafted mice with (right) or without (left) CRH loading.
FIGS. 5e and 5f show increased productions of ACTH (e) and corticosterone (f) by CRH loading.
FIGS. 5g and 5h show basal levels of ACTH- and corticosterone-production without CRH loading.
FIGS. 5i and 5j show improvement of spontaneous locomotor activity in hypophysectomized mice by the transplantation of ACTH-producing cells.
FIG. 5k shows survival of hypophysectomized mice transplanted with aggregates, analyzed by Kaplan-Meyer method.

The ES cell-derived ACTH-positive cells transplanted under renal capsule were confirmed to have topically engrafted even 7 days after the transplantation by histochemical staining by the fluorescence antibody method (FIG. 5a, left). In the control group (sham operation), blood ACTH was less than 1 pg/ml and Corticosteron was less than 3 pg/ml even after CRH loading. In contrast, in the ES cell-derived ACTH-positive cells transplantation group, ACTH reached the concentration of 25-30 pg/ml and Corticosteron reached the concentration of 300 pg/ml after CRH loading (FIGS. 5e, f: with CRH loading; FIGS. 5 g, h: without CRH loading).

Example 7: Improvement of Survival and Activity of Hypophysectomized Mice by Ectopic Transplantation of ES Cell-Derived ACTH-Positive Cells (Method)

In the same manner as in Example 6, mouse ES cell-derived ACTH-producing cells were transplanted under renal capsule of hypophysectomized mouse (9-week-old).

Survival of and an increase in the body weight of the transplanted mouse were observed and compared with those of the control group (sham operation). The spontaneous movement of the mouse was also examined. As the spontaneous movement of the mouse, how much the mouse spontaneously moves in a cage for one day was measured using an IR sensor (MDC-WO2 (BrainScienceIdea, Osaka)). In addition, using ENV-044 (MedAssociates, Georgia), how many times the mouse spontaneously rotated a running wheel for one day was separately measured.
(Results)
While the hypophysectomized mice in the control group all died by 8 weeks after the sham operation, about 85% of the animals in the ES cell-derived ACTH-producing cells transplantation group was alive at that time point (FIG. 5k). In addition, at the stage of 8 weeks when all died in the control group, 60% of mice in the transplantation group gained weight than at the time of transplantation.

In addition, the mice in the transplantation group showed a higher level of spontaneous movement than the control (FIGS. 5i, j).

Figure 7:
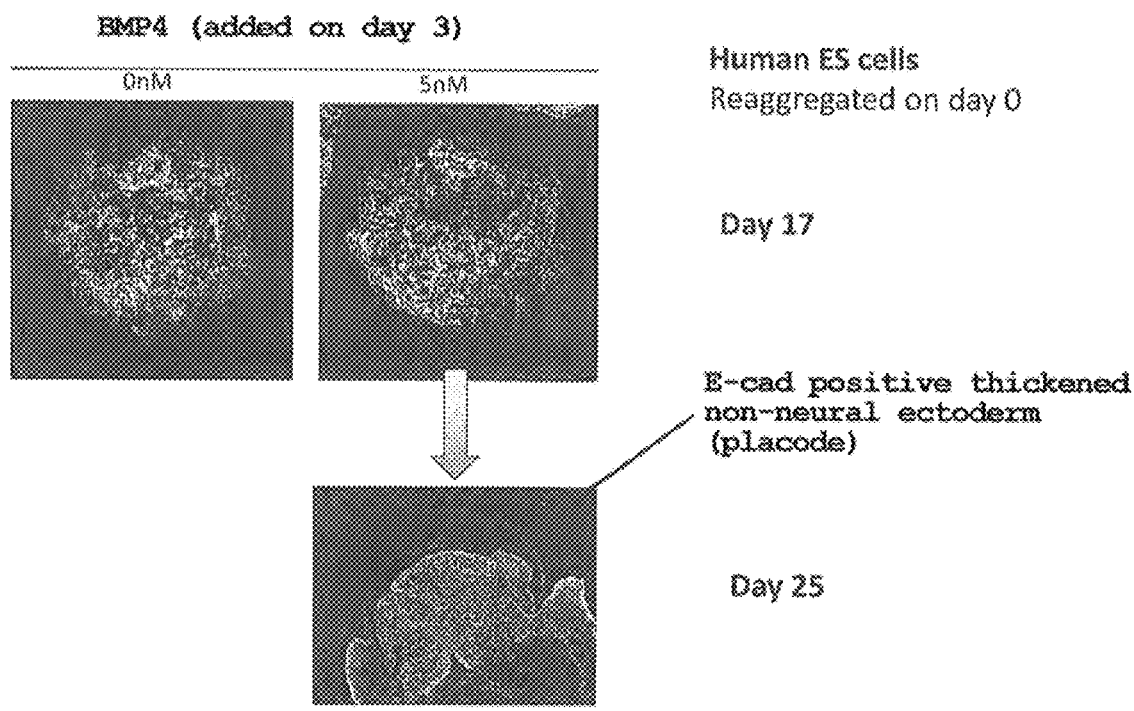
FIG. 7 shows the results of floating aggregates culture using human ES cells at 12000 cells/aggregate. In the aggregates added with 5 nM BMP4 on day 3 of culture, aggregates wherein Rx$^+$ rostral hypothalamus tissue cells are encapsulated by a monolayer sheeted continuous epithelium composed of E-cadherin$^+$ rostral non-neural head ectoderm tissues were formed on day 17 of culture. Furthermore, formation of E-cadherin$^+$ thickened non-neural ectoderm was found on day 25 of culture.
Figure 8:
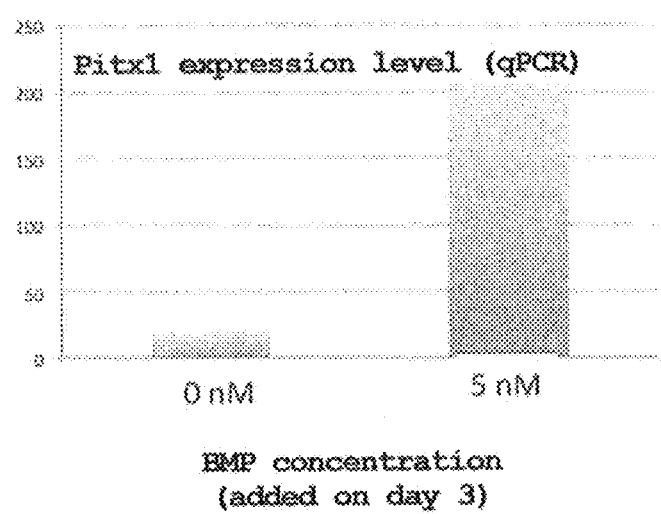
FIG. 8 shows the measurement results of mRNA expression of Pitx1, a marker of a rostral non-neural head ectoderm tissue, by quantitative PCR using cell aggregates on day 17 of culture in FIG. 7. In the aggregates added with 5 nM BMP4, the mRNA expression of Pitx1 increased about 10-folds as compared to the aggregates without the addition.

Example 8: Differentiation Induction of Human ES Cell into Pituitary Progenitor Cell (Method)
Human ES cells (12000 cells) dispersed into single-cells with trypsin were subjected to floating aggregate culture in the presence of a 10 µM ROCK inhibitor Y-27632 (Watanabe et al, Nature Neuroscience, 2007) in the same manner as in Example 1. The culture medium used was gfCDM added with 5% KSR. From day 3 of culture, 0.5 nM, 1.5 nM or 5.0 nM BMP4 was added to the culture medium, 1000 nM SAG was added from day 6 of culture, and the floating-culture was continued.
(Results)
On day 17 of culture, all aggregates comprised many Rx-positive neural precursor cells in the aggregates, and E-cad and cytokeratin-positive non-neural ectoderm cells formed a sheet-like epithelial structure composed of the monolayer cells on the surface thereof, in the same manner as in the culture of mouse ES cells (FIG. 7). By qPCR analysis, the expression of Pitx1 was induced about 10-fold in the group treated with 5 nM BMP as compared with the group without the treatment (FIG. 8). The group treated with BMP comprised E-cad positive non-neural ectoderm on the surface of a Rx-positive neuroepithelial structure on day 25 of culture and, in the same manner as in the pituitary placode formation in the mouse culture, a part thereof was thickened to show a placode-like structure (FIG. 7).

Even when started from human ES cells (3000 cells and 6000 cells) dispersed into single-cells with trypsin, equivalent results were obtained. Therefore, the possibility of induction of simultaneous differentiation into both a rostral hypothalamus tissue and a rostral non-neural head ectodermal tissue which is a sheet-like continuous epithelium was shown even when aggregates composed of a comparatively small number of cells are used, by adding BMP4 to the medium.

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

The contents disclosed in any publication cited herein, including patents and patent applications, are hereby incorporated in their entireties by reference, to the extent that they have been disclosed herein.

INDUSTRIAL APPLICABILITY

According to the method of the present invention, differentiation of pluripotent stem cells such as ES cells and the like into aggregates comprising a central nervous tissue and a non-neural head ectodermal tissue, particularly aggregates comprising a rostral hypothalamus tissue and a rostral head ectodermal tissue and pituitary precursor tissue can be induced in vitro, and differentiation into various pituitary hormone-producing cells can be induced. Pituitary gland is a central endocrine organ that produces and secretes many hormones, and abnormal hormone secretion exerts a grave influence on the live body. Therefore, the aggregate, pituitary precursor tissue and pituitary hormone producing cells obtained by the method of the present invention can be particularly utilized for the treatment and the like of the diseases caused by the deficiency of secretion of pituitary hormones and the diseases causing deficiency of a pituitary hormone secretion.

Not only pituitary but also sensory placodes such as olfactory epithelium, crystalline lens, inner ear and the like can be formed from the aggregates comprising a central nervous tissue and a non-neural head ectodermal tissue.

This application is based on a patent application No. 2011-239803 filed in Japan (filing date: Oct. 31, 2011), the contents of which are incorporated in full herein.

The invention claimed is:

1. A method of producing an aggregate comprising both a central nervous tissue and a non-neural head ectodermal tissue, comprising
 a step of forming an aggregate of stem cells in a serum-free medium, and
 a step of floating-culturing the formed aggregate in a serum-free medium,
 wherein a Shh signal promoter and a BMP signal promoter are added to the serum-free medium used for the floating-culturing,
 wherein the Shh signal promoter is SAG and is added within 192 hours from the start of the floating-culture at a concentration of 50-1000 nM, and
 wherein the BMP signal promoter is BMP2 and/or BMP4 and is added within 96 hours from the start of the floating-culture at a concentration of 0.5-5 nM,
 thereby producing an aggregate comprising both a central nervous tissue and a non-neural head ectodermal tissue.

2. The production method according to claim 1, wherein the BMP signal promoter is added after 48 hours and within 96 hours from the start of the floating-culture.

3. A method of producing an aggregate comprising both a hypothalamus tissue and a non-neural head ectoderm, comprising
 a step of forming an aggregate of stem cells in a serum-free medium, and
 a step of floating-culturing the formed aggregate in a serum-free medium,
 wherein a Shh signal promoter and a BMP signal promoter are added to the serum-free medium used for the floating-culturing,
 wherein the Shh signal promoter is SAG and is added within 192 hours from the start of the floating-culture at a concentration of 50-1000 nM, and wherein the BMP signal promoter is BMP2 and/or BMP4 and is added within 96 hours from the start of the floating-culture at a concentration of 0.5-5 nM, thereby producing an aggregate comprising both a hypothalamus tissue and a non-neural head ectoderm.

4. The production method according to claim 3, wherein the hypothalamus tissue and non-neural head ectoderm are a rostral hypothalamus tissue and a rostral non-neural head ectodermal tissue which is a sheet-like continuous epithelium.

5. The production method according to claim 4, wherein the rostral hypothalamus tissue is Rx-positive.

6. The production method according to claim 4, wherein the rostral non-neural head ectodermal tissue which is a sheet-like continuous epithelium is Pitx1-positive.

7. The method according to claim 3, wherein the serum-free medium in the floating-culturing step does not substantially comprise a Nodal signal promoter, a Wnt signal promoter, an FGF signal promoter, retinoic acid and insulin.

8. The production method according to claim 3, wherein the stem cells are derived from human.

9. The production method according to claim 3, wherein the aggregate comprising both a hypothalamus tissue and a non-neural head ectoderm further comprises Lim3-positive cells.

10. The production method according to claim 9, wherein the Lim3-positive cells form an epithelial pouch vesicle in the aggregate.

11. The production method according to claim 3, wherein the BMP signal promoter is added after 48 hours and within 96 hours from the start of the floating-culture.

12. A method of producing an adrenocorticotropic hormone-producing cell, comprising
(i) a step of producing an aggregate comprising both a hypothalamus tissue and a non-neural head ectoderm by the production method according to claim 3, and
(ii) a step of further floating-culturing the aggregate obtained in step (i) in a serum-free medium comprising a Notch signal inhibitor.

13. The production method according to claim 12, wherein the Notch signal inhibitor is DAPT.

14. A method of producing a growth hormone-producing cell, comprising
(i) a step of producing an aggregate comprising both a hypothalamus tissue and a non-neural head ectoderm by the production method according to claim 3, and
(ii) a step of further floating-culturing the aggregate obtained in step (i) in a serum-free medium comprising glucocorticoid.

15. The production method according to claim 14, wherein the serum-free medium in step (ii) further comprises insulin.

16. The production method according to claim 14, comprising a step of floating-culturing the aggregate comprising both a hypothalamus tissue and a non-neural head ectoderm in a serum-free medium comprising a GSK3β inhibitor before or simultaneously with the step of floating-culturing in a serum-free medium comprising glucocorticoid.

17. The production method according to claim 16, wherein the GSK3β inhibitor is BIO.

18. A method of producing a prolactin-producing cell, comprising
(i) a step of producing an aggregate comprising both a hypothalamus tissue and a non-neural head ectoderm by the production method according to claim 3, and
(ii) a step of further floating-culturing the aggregate obtained in step (i) in a serum-free medium comprising an estrogen.

19. The production method according to claim 18, wherein the serum-free medium in step (ii) further comprises insulin.

20. The production method according to claim 18, comprising a step of floating-culturing the aggregate comprising both a hypothalamus tissue and a non-neural head ectoderm in a serum-free medium comprising a GSK3β inhibitor before or simultaneously with the step of floating-culturing in a serum-free medium comprising an estrogen.

21. The production method according to claim 20, wherein the GSK3β inhibitor is BIO.

22. A method of producing a follicle-stimulating hormone-, luteinizing hormone- and/or thyroid-stimulating hormone-producing cell, comprising
(i) a step of producing an aggregate comprising both a hypothalamus tissue and a non-neural head ectoderm by the production method according to claim 3, and
(ii) a step of further floating-culturing the aggregate obtained in step (i) in a stromal cell-conditioned medium obtained by cultivating stromal cells in a serum-free medium.

23. The production method according to claim 22, wherein the stromal cell is PA6 cell.

24. A method of producing an aggregate comprising both a hypothalamus tissue and a non-neural head ectoderm, comprising
(1) forming an aggregate of stem cells in a serum-free medium,
(2) floating-culturing the formed aggregate in a serum-free medium,
wherein a Shh signal promoter and a BMP signal promoter are added to the serum-free medium used for the floating-culturing,
wherein the Shh signal promoter is SAG and is added within 192 hours from the start of the floating-culture at a concentration of 50-1000 nM, and
wherein the BMP signal promoter is BMP2 and/or BMP4 and is added within 96 hours from the start of the floating-culture at a concentration of 0.5-5 nM,
thereby obtaining an aggregate that comprises Rx-positive neural precursor cells and E-cad and cytokeratin-positive non-neural ectoderm cells, the neural precursor cells being present in the aggregate, and the non-neural ectoderm cells being present on the surface of the aggregate and forming an epithelial structure, and
(3) floating-culturing the aggregate obtained in (2) in a serum-free medium containing SAG, thereby obtaining an aggregate comprising both a hypothalamus tissue and a non-neural head ectoderm.

* * * * *